(12) United States Patent
Higashi

(10) Patent No.: US 10,130,634 B2
(45) Date of Patent: Nov. 20, 2018

(54) THERAPEUTIC AGENT FOR OPHTHALMIC DISEASE

(71) Applicant: MITSUBISHI TANABE PHARMA CORPORATION, Osaka (JP)

(72) Inventor: Hidemitsu Higashi, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 4 days.

(21) Appl. No.: 14/906,355

(22) PCT Filed: Jul. 24, 2014

(86) PCT No.: PCT/JP2014/069507
§ 371 (c)(1),
(2) Date: Jan. 20, 2016

(87) PCT Pub. No.: WO2015/012332
PCT Pub. Date: Jan. 29, 2015

(65) Prior Publication Data
US 2016/0193217 A1 Jul. 7, 2016

(30) Foreign Application Priority Data
Jul. 24, 2013 (JP) ................................. 2013-153878

(51) Int. Cl.
| | |
|---|---|
| A61K 31/535 | (2006.01) |
| A61K 31/5377 | (2006.01) |
| C07D 413/12 | (2006.01) |
| C07D 417/12 | (2006.01) |
| C07D 417/14 | (2006.01) |
| C07D 265/30 | (2006.01) |
| C07D 513/04 | (2006.01) |
| A61K 31/5375 | (2006.01) |

(52) U.S. Cl.
CPC ...... *A61K 31/5377* (2013.01); *A61K 31/5375* (2013.01); *C07D 265/30* (2013.01); *C07D 413/12* (2013.01); *C07D 417/12* (2013.01); *C07D 417/14* (2013.01); *C07D 513/04* (2013.01)

(58) Field of Classification Search
CPC .................................................... A61K 31/535
USPC ..................................................... 514/236.8
See application file for complete search history.

(56) References Cited

U.S. PATENT DOCUMENTS

| | | | | |
|---|---|---|---|---|
| 7,935,700 B2* | 5/2011 | Tanaka | ................. | C07D 265/30 514/236.8 |
| 8,008,092 B2* | 8/2011 | Ambati | ................. | A61K 31/195 424/139.1 |
| 2007/0265237 A1* | 11/2007 | Mendez | ................. | C07J 43/003 514/176 |
| 2007/0265257 A1* | 11/2007 | Tanaka | ................. | C07D 265/30 514/231.5 |
| 2009/0123375 A1* | 5/2009 | Ambati | ................. | A61K 31/195 514/1.1 |
| 2009/0264430 A1 | 10/2009 | Masuda et al. | | |
| 2010/0261687 A1* | 10/2010 | Grundl | ............... | A61K 31/4523 514/171 |
| 2012/0087928 A1* | 4/2012 | Lashkari | ............ | G01N 33/6863 424/158.1 |

FOREIGN PATENT DOCUMENTS

| | | |
|---|---|---|
| WO | 2006/028284 | 3/2006 |
| WO | 2008/007691 | 1/2008 |
| WO | 2013/079696 | 6/2013 |

OTHER PUBLICATIONS

WebMD Macular Degeneration Treatment Page (published 2007).*
Takeda and coworkers (Nature vol. 460 pp. 225-230 published 2009).*
Takeda et al, Nature vol. 460 pp. 225-230 published 2009 (Year: 2009).*
Takeda et al, (Nature, vol. 460 pp. 225-230 published 2009). (Year: 2009).*
Written Opinion of the International Searching Authority dated Sep. 9, 2014 in International Application No. PCT/JP2014/069507 (English translation).
International Search Report dated Sep. 9, 2014 in International Application No. PCT/JP2014/069507 (English translation).

* cited by examiner

*Primary Examiner* — Timothy P Thomas
*Assistant Examiner* — George W Kosturko
(74) *Attorney, Agent, or Firm* — Wenderoth, Lind & Ponack, L.L.P.

(57) ABSTRACT

The present invention provides a therapeutic agent or prophylactic agent for an ophthalmic disease caused by ocular angiogenesis, which contains a morpholine compound represented by the formula (1)

(1)

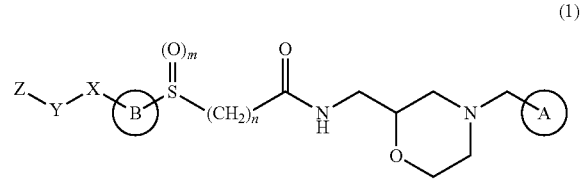

wherein ring A is aryl optionally having substituent(s) and the like; ring B is arylene optionally having substituent(s) and the like; m=0-2; n=1-5; X is a bond and the like; Y is a bond and the like; and Z is a hydrogen atom and the like, or a pharmaceutically acceptable salt thereof as an active ingredient.

10 Claims, 1 Drawing Sheet

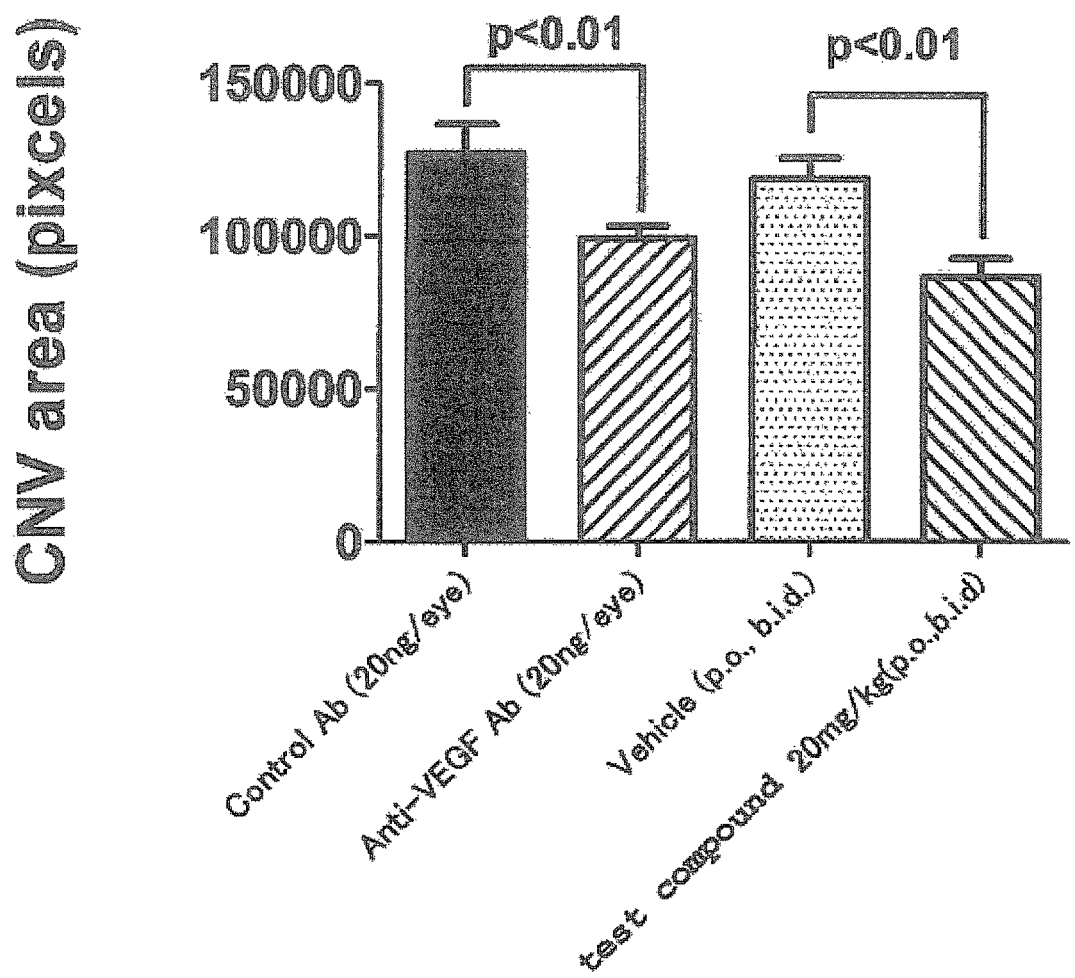

THERAPEUTIC AGENT FOR OPHTHALMIC DISEASE

TECHNICAL FIELD

The present invention relates to a therapeutic agent or prophylactic agent for an ophthalmic disease caused by ocular angiogenesis, which contains a morpholine compound or a pharmaceutically acceptable salt thereof as an active ingredient.

BACKGROUND ART

Angiogenesis is known to exert a large influence on the wound therapy and progress of many diseases. As ophthalmic diseases involving angiogenesis, retinopathy of prematurity, diabetic retinopathy, age-related macular degeneration, neovascular glaucoma and the like are known. In addition, corneal neovascularization due to various stimulations on and invasions into the cornea is also known. In these diseases, angiogenesis lacking a control mechanism occurs. Vascular endothelial growth factors (VEGF) are involved in angiogenesis, and anti-VEGF antibodies such as bevacizumab as well as sorafenib, sunitinib, pegaptanib sodium, ranibizumab, aflibercept, and VEGF-Trap EYE and the like are known as anti-VEGF drugs. Medicaments targeting VEGF are widely used clinically for the treatment of ophthalmic diseases such as age-related macular degeneration, branch retinal vein occlusion, central retinal vein occlusion, diabetic maculopathy, diabetic retinopathy, and neovascular glaucoma and the like. However, since the aforementioned anti-VEGF drugs are administered by intravitreal injection to reduce systemic side effects, a heavy burden is imposed on the patients, and the lens and retinal tissues are constantly exposed to the risk of ocular tissue damage during injection, and bacterial infection. VEGF has various activities such as maintenance of normal choroidal blood vessel homeostasis (e.g., non-patent document 1: Proc. Natl. Acad. Sci., 2009, 106: 18751-18756), action as a nutritional factor of retinal nerve cells (e.g., non-patent document 2: Am. J. Patho., 2007, 171: 53-67) and the like, and the possibility that a long-term inhibition of VEGF may provide an adverse influence on the ocular tissues cannot be denied. Therefore, the development of a treatment method targeting a molecule other than VEGF and selectively effective for angiogenesis is one of the problems. In recent years, it is known that chemokine, which is one of the cell chemotactic factors, induces angiogenesis (non-patent document 3: Arterioscler. Thromb. Vasc. Biol., 2008, 28: 1928-1936). Particularly, CCL11 in the CC chemokine family is known to induce migration of vascular endothelial cells and angiogenesis in vivo model, by a signal via CCR3, which is a receptor thereof (non-patent document 4: J. Immunology, 2001, 166: 7571-7578). CCR3 is known as a chemokine receptor of eosinophils, and antagonists thereof have been studied as treatment targets of allergic diseases such as asthma, allergic rhinitis and atopic dermatitis (non-patent document 5: Medicinal Research Reviews, 2010, 30: 778-817). However, it has been clarified that CCR3 is specifically expressed in vascular endothelial cells of choroidal new blood vessels with age-related macular degeneration, and involved in the progress thereof (non-patent document 6: Nature, 2009, 460: 225-230). In addition, a patent application describing that 4-[[[[[[(2S)-4-[(3,4-dichlorophenyl) methyl]-2-morpholinyl]methyl]-amino]carbonyl]amino] methyl]benzamide, which is a CCR3 antagonist, is useful for neovascular age related macular degeneration has been published (patent document 1: WO 2013/079696). In addition, it has been reported that expression of CCR3 is found in choroidal vascular endothelial cells in choroidal neovascularization found in eye histoplasmosis syndrome (non-patent document 7: Invest. Ophthalmol. Vis. Sci., 2010, 51: E-Abstract 3351), and expression of CCR3 is found in the corneal neovascularization site of a corneal neovascularization model due to corneal injury (non-patent document 8: Int. J. Ophthalmol., 2012, 5: 251-257). Furthermore, it has been recently reported that CCR3 is expressed in the vascular endothelium of a proliferative membrane isolated from proliferative diabetic retinopathy (non-patent document 9: Japanese Journal of Ophthalmology 2013 vol. 117, Extra issue, Abstract No. P-140). Therefore, a low-molecular-weight compound showing a CCR3 antagonistic action can treat and/or prevent ocular angiogenesis by a mechanism different from that of an anti-VEGF drug.

On the other hand, a morpholine compound represented by the following formula (1)

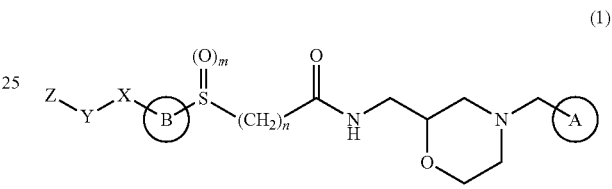

(1)

[wherein
ring A is aryl optionally having substituent(s), or heteroaryl optionally having substituent(s),
ring B is arylene optionally having substituent(s), a divalent heterocyclic group optionally having substituent(s), or $C_{3-8}$ cycloalkylene optionally having substituent(s),
m is an integer of 0 to 2,
n is an integer of 1 to 5,
X is a bond, —NH—, —NR$^1$— (wherein R$^1$ is $C_{1-6}$ alkyl optionally having substituent(s)), —CO—, —CO$_2$—, —OCO—, —CONR$^a$— (wherein R$^a$ is a hydrogen atom or $C_{1-6}$ alkyl optionally having substituent(s), hereinafter the same), —NR$^a$CO—, —NR$^2$CONR$^3$— (wherein R$^2$ and R$^3$ are the same or different and each is a hydrogen atom or $C_{1-6}$ alkyl optionally having substituent(s), or R$^2$ and R$^3$ are optionally joined to form, together with atoms bonded thereto, a ring optionally having substituent(s)), an oxygen atom, a sulfur atom, —SO—, —SO$_2$—, —NR$^a$SO$_2$—, —SO$_2$NR$^a$—, $C_{1-6}$ alkylene optionally having substituent(s), $C_{2-6}$ alkenylene optionally having substituent(s), $C_{2-6}$ alkynylene optionally having substituent(s), —O—X$^a$— (wherein X$^a$ is $C_{1-6}$ alkylene optionally having substituent(s), hereinafter the same), —X$^a$—O—, —CO—X$^a$—, —X$^a$—CO—, —CONR$^a$—X$^a$—, —X$^a$—CONR$^a$—, —NR$^a$CO—X$^a$—, —X$^a$—NR$^a$CO—, —S—X$^a$—, —X$^a$—S—, —SO—X$^a$—, —X$^a$—SO—, —NR$^a$—X$^a$—, —X$^a$—NR$^a$—, —SO$_2$—X$^a$—, —X$^a$—SO$_2$—, —C(=N—CO$_2$—R$^1$)—, —C(=N—SO$_2$—R$^1$)—, —C(=N—SO$_2$NH$_2$)—, —C(=CH—NO$_2$)—, —C(=N—CN)— or $C_{3-8}$ cycloalkylidene optionally having substituent(s),
Y is a bond, —NH—, —NR$^4$— (wherein R$^4$ is $C_{1-6}$ alkyl optionally having substituent(s), hereinafter the same), —CO—, —CO$_2$—, —OCO—, —CONR$^b$— (wherein R$^b$ is a hydrogen atom or $C_{1-6}$ alkyl optionally having substituent(s), hereinafter the same), —NR$^b$CO—, —NR$^5$CONR$^6$— (wherein R$^5$ and R$^6$ are the same or different and each is a hydrogen atom or $C_{1-6}$ alkyl optionally having substituent(s), or $R^5$ and $R^6$ are optionally joined to form, together with atoms bonded thereto, a ring optionally having substituent(s)), an oxygen atom, a sulfur atom, —SO—, —SO$_2$—, —NR$^b$SO$_2$—, —SO$_2$NR$^b$—, $C_{1-6}$ alkylene optionally having substituent(s), $C_{2-6}$ alkenylene optionally having substituent(s), $C_{2-6}$ alkynylene optionally having substituent(s), —O—X$^b$— (wherein X$^b$ is $C_{1-6}$ alkylene optionally having substituent(s), hereinafter the same), —X$^b$—O—, —CO—X$^b$—, —X$^b$—CO—, —CONR$^b$—X$^b$—, —X$^b$—CONR$^b$—, —NR$^b$CO—X$^b$—, —X$^b$—NR$^b$CO—, —S—X$^b$—, —X$^b$—S—, —SO—X$^b$—, —X$^b$—SO—, —NR$^b$—X$^b$—, —X$^b$—NR$^b$—, —SO$_2$—X$^b$—, —X$^b$—SO$_2$—, —C(=N—CO$_2$—R$^4$)—, —C(=N—SO$_2$—R$^4$)—, —C(=N—SO$_2$NH$_2$)—, —C(=CH—NO$_2$)— or —C(=N—CN)—, and Z is a hydrogen atom, a halogen atom, $C_{1-6}$ alkyl optionally having substituent(s), $C_{3-8}$ cycloalkyl optionally having substituent(s), aryl optionally having substituent(s), a heterocyclic group optionally having substituent(s), hydroxy, nitro, amino, cyano, $C_{1-6}$ alkoxy optionally having substituent(s), mono- or di-$C_{1-6}$ alkylamino optionally having substituent(s), $C_{1-7}$ acylamino optionally having substituent(s), sulfonylamino optionally having substituent(s), hydrazino optionally having substituent(s), guanidino optionally having substituent(s) or amidino optionally having substituent(s)], or a pharmaceutically acceptable salt thereof is a compound having a CCR3 antagonistic action, which is described in WO pamphlets of WO 2006/028284 (patent document 2) and WO 2008/007691 (patent document 3). However, there is no prior art document that describes or suggests that such morpholine compound treats and/or prevents ocular angiogenesis.

DOCUMENT LIST

Patent Documents patent document 1: WO 2013/079696
patent document 2: WO 2006/028284
patent document 3: WO 2008/007691

Non-Patent Documents non-patent document 1: Proc. Natl. Acad. Sci., 2009, 106: 18751-18756
non-patent document 2: Am. J. Patho., 2007, 171: 53-67
non-patent document 3: Arterioscler. Thromb. Vasc. Biol., 2008, 28: 1928-1936
non-patent document 4: J. Immunology, 2001, 166: 7571-7578
non-patent document 5: Medicinal Research Reviews, 2010, 30: 778-817
non-patent document 6: Nature, 2009, 460: 225-230
non-patent document 7: Invest. Ophthalmol. Vis. Sci., 2010, 51: E-Abstract 3351
non-patent document 8: Int. J. Ophthalmol., 2012, 5: 251-257
non-patent document 9: Japanese Journal of Ophthalmology 2013 vol. 117, Extra issue, Abstract No. P-140

SUMMARY OF THE INVENTION

Problems to be Solved by the Invention

The present invention aims to provide a therapeutic agent or prophylactic agent for an ophthalmic disease caused by ocular angiogenesis, which contains a morpholine compound or a pharmaceutically acceptable salt thereof as an active ingredient.

Means of Solving the Problems

The present inventors have found that a morpholine compound represented by the above-mentioned formula (1) or a pharmaceutically acceptable salt thereof showing a CCR3 antagonistic action acts as a therapeutic agent or prophylactic agent for an ophthalmic disease caused by ocular angiogenesis, which resulted in the completion of the present invention.

That is, the gist of the present invention is as described below.

[1] A therapeutic agent or prophylactic agent for an ophthalmic disease caused by ocular angiogenesis, which comprises, as an active ingredient, a morpholine compound represented by the formula (1)

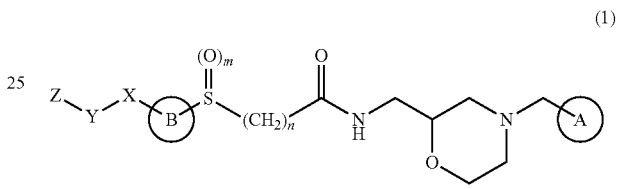

(1)

[wherein
ring A is aryl optionally having substituent(s), or heteroaryl optionally having substituent(s),
ring B is arylene optionally having substituent(s), a divalent heterocyclic group optionally having substituent(s), or $C_{3-8}$ cycloalkylene optionally having substituent(s),
m is an integer of 0 to 2,
n is an integer of 1 to 5,
X is a bond, —NH—, —NR$^1$— (wherein R$^1$ is $C_{1-6}$ alkyl optionally having substituent(s)), —CO—, —CO$_2$—, —OCO—, —CONR$^a$— (wherein R$^a$ is a hydrogen atom or $C_{1-6}$ alkyl optionally having substituent(s), hereinafter the same), —NR$^a$CO—, —NR$^2$CONR$^3$— (wherein R$^2$ and R$^3$ are the same or different and each is a hydrogen atom or $C_{1-6}$ alkyl optionally having substituent(s), or R$^2$ and R$^3$ are optionally joined to form, together with atoms bonded thereto, a ring optionally having substituent(s)), an oxygen atom, a sulfur atom, —SO—, —SO$_2$—, —NR$^a$SO$_2$—, —SO$_2$NR$^a$—, $C_{1-6}$ alkylene optionally having substituent(s), $C_{2-6}$ alkenylene optionally having substituent(s), $C_{2-6}$ alkynylene optionally having substituent(s), —O—X$^a$— (wherein X$^a$ is $C_{1-6}$ alkylene optionally having substituent(s), hereinafter the same), —X$^a$—O—, —CO—X$^a$—, —X$^a$—CO—, —CONR$^a$—X$^a$—, —X$^a$—CONR$^a$—, —NR$^a$CO—X$^a$—, —X$^a$—NR$^a$CO—, —S—X$^a$—, —X$^a$—S—, —SO—X$^a$—, —X$^a$—SO—, —NR$^a$—X$^a$—, —X$^a$—NR$^a$—, —SO$_2$—X$^a$—, —X$^a$—SO$_2$—, —C(=N—CO$_2$—R$^1$)—, —C(=N—SO$_2$—R$^1$)—, —C(=N—SO$_2$NH$_2$)—, —C(=CH—NO$_2$)—, —C(=N—CN)— or $C_{3-8}$ cycloalkylidene optionally having substituent(s),
Y is a bond, —NH—, —NR$^4$— (wherein R$^4$ is $C_{1-6}$ alkyl optionally having substituent(s), hereinafter the same), —CO—, —CO$_2$—, —OCO—, —CONR$^b$— (wherein R$^b$ is a hydrogen atom or $C_{1-6}$ alkyl optionally having substituent(s), hereinafter the same), —NR$^b$CO—, —NR$^5$CONR$^6$— (wherein R$^5$ and R$^6$ are the same or different and each is a hydrogen atom or $C_{1-6}$ alkyl optionally having substituent(s), or $R^5$ and $R^6$ are optionally joined to form, together with atoms bonded thereto, a ring optionally having substituent(s)), an oxygen atom, a sulfur atom, —SO—, —SO$_2$—, —NR$^b$SO$_2$—, —SO$_2$NR$^b$—, $C_{1-6}$ alkylene optionally having substituent(s), $C_{2-6}$ alkenylene optionally having substituent(s), $C_{2-6}$ alkynylene optionally having substituent(s), —O—X$^b$— (wherein X$^b$ is $C_{1-6}$ alkylene optionally having substituent(s), hereinafter the same), —X$^b$—O—, —CO—X$^b$—, —X$^b$—CO—, —CONR$^b$—X$^b$—, —X$^b$—CONR$^b$—, —NR$^b$CO—X$^b$—, —X$^b$—NR$^b$CO—, —S—X$^b$—, —X$^b$—S—, —SO—X$^b$—, —X$^b$—SO—, —NR$^b$—X$^b$—, —X$^b$—NR$^b$—, —SO$_2$—X$^b$—, —X$^b$—SO$_2$—, —C(=N—CO$_2$—R$^4$)—, —C(=N—SO$_2$—R$^4$)—, —C(=N—SO$_2$NH$_2$)—, —C(=CH—NO$_2$)— or —C(=N—CN)—, and Z is a hydrogen atom, a halogen atom, $C_{1-6}$ alkyl optionally having substituent(s), $C_{3-8}$ cycloalkyl optionally having substituent(s), aryl optionally having substituent(s), a heterocyclic group optionally having substituent(s), hydroxy, nitro, amino, cyano, $C_{1-6}$ alkoxy optionally having substituent(s), mono- or di-$C_{1-6}$ alkylamino optionally having substituent(s), $C_{1-7}$ acylamino optionally having substituent(s), sulfonylamino optionally having substituent(s), hydrazino optionally having substituent(s), guanidino optionally having substituent(s) or amidino optionally having substituent(s)], or a pharmaceutically acceptable salt thereof.

[2] A method of treating or preventing an ophthalmic disease caused by ocular angiogenesis, comprising administering an effective amount of a morpholine compound represented by the formula (1)

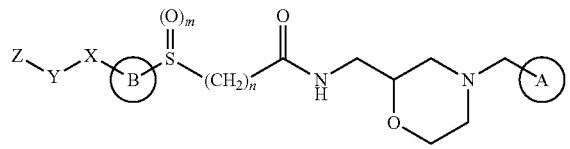

(1)

[wherein
ring A is aryl optionally having substituent(s), or heteroaryl optionally having substituent(s),
ring B is arylene optionally having substituent(s), a divalent heterocyclic group optionally having substituent(s), or $C_{3-8}$ cycloalkylene optionally having substituent(s),
m is an integer of 0 to 2,
n is an integer of 1 to 5,
X is a bond, —NH—, —NR$^1$— (wherein $R^1$ is $C_{1-6}$ alkyl optionally having substituent(s)), —CO—, —CO$_2$—, —OCO—, —CONR$^a$— (wherein $R^a$ is a hydrogen atom or $C_{1-6}$ alkyl optionally having substituent(s), hereinafter the same), —NR$^a$CO—, —NR$^2$CONR$^3$— (wherein $R^2$ and $R^3$ are the same or different and each is a hydrogen atom or $C_{1-6}$ alkyl optionally having substituent(s), or $R^2$ and $R^3$ are optionally joined to form, together with atoms bonded thereto, a ring optionally having substituent(s)), an oxygen atom, a sulfur atom, —SO—, —SO$_2$—, —NR$^a$SO$_2$—, —SO$_2$NR$^a$—, $C_{1-6}$ alkylene optionally having substituent(s), $C_{2-6}$ alkenylene optionally having substituent(s), $C_{2-6}$ alkynylene optionally having substituent(s), —O—X$^a$— (wherein X$^a$ is $C_{1-6}$ alkylene optionally having substituent(s), hereinafter the same), —X$^a$—O—, —CO—X$^a$—, —X$^a$—CO—, —CONR$^a$—X$^a$—, —X$^a$—CONR$^a$—, —NR$^a$CO—X$^a$—, —X$^a$—NR$^a$CO—, —S—X$^a$—, —X$^a$—S—, —SO—X$^a$—, —X$^a$—SO—, —NR$^a$—X$^a$—, —X$^a$—NR$^a$—, —SO$_2$—X$^a$—, —X$^a$—SO$_2$—, —C(=N—CO$_2$—R$^1$)—, —C(=N—SO$_2$—R)—, —C(=N—SO$_2$NH$_2$)—, —C(=CH—NO$_2$)—, —C(=N—CN)— or $C_{3-8}$ cycloalkylidene optionally having substituent(s), Y is a bond, —NH—, —NR$^4$— (wherein $R^4$ is $C_{1-6}$ alkyl optionally having substituent(s), hereinafter the same), —CO—, —CO$_2$—, —OCO—, —CONR$^b$— (wherein $R^b$ is a hydrogen atom or $C_{1-6}$ alkyl optionally having substituent(s), hereinafter the same), —NR$^b$CO—, —NR$^5$CONR$^6$— (wherein $R^5$ and $R^6$ are the same or different and each is a hydrogen atom or $C_{1-6}$ alkyl optionally having substituent(s), or $R^5$ and $R^6$ are optionally joined to form, together with atoms bonded thereto, a ring optionally having substituent(s)), an oxygen atom, a sulfur atom, —SO—, —SO$_2$—, —NR$^b$SO$_2$—, —SO$_2$NR$^b$—, $C_{1-6}$ alkylene optionally having substituent(s), $C_{2-6}$ alkenylene optionally having substituent(s), $C_{2-6}$ alkynylene optionally having substituent(s), —O—X$^b$— (wherein X$^b$ is $C_{1-6}$ alkylene optionally having substituent(s), hereinafter the same), —X$^b$—O—, —CO—X$^b$—, —X$^b$—CO—, —CONR$^b$—X$^b$—, —X$^b$—CONR$^b$—, —NR$^b$CO—X$^b$—, —X$^b$—NR$^b$CO—, —S—X$^b$—, —X$^b$—S—, —SO—X$^b$—, —X$^b$—SO—, —NR$^b$—X$^b$—, —X$^b$—NR$^b$—, —SO$_2$—X$^b$—, —X$^b$—SO$_2$—, —C(=N—CO$_2$—R$^4$)—, —C(=N—SO$_2$—R$^4$)—, —C(=N—SO$_2$NH$_2$)—, —C(=CH—NO$_2$)— or —C(=N—CN)—, and Z is a hydrogen atom, a halogen atom, $C_{1-6}$ alkyl optionally having substituent(s), $C_{3-8}$ cycloalkyl optionally having substituent(s), aryl optionally having substituent(s), a heterocyclic group optionally having substituent(s), hydroxy, nitro, amino, cyano, $C_{1-6}$ alkoxy optionally having substituent(s), mono- or di-$C_{1-6}$ alkylamino optionally having substituent(s), $C_{1-7}$ acylamino optionally having substituent(s), sulfonylamino optionally having substituent(s), hydrazino optionally having substituent(s), guanidino optionally having substituent(s) or amidino optionally having substituent(s)], or a pharmaceutically acceptable salt thereof to an animal.

[3] Use of a morpholine compound represented by the formula (1)

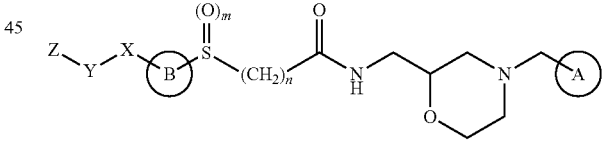

(1)

[wherein
ring A is aryl optionally having substituent(s), or heteroaryl optionally having substituent(s),
ring B is arylene optionally having substituent(s), a divalent heterocyclic group optionally having substituent(s), or $C_{3-8}$ cycloalkylene optionally having substituent(s),
m is an integer of 0 to 2,
n is an integer of 1 to 5,
X is a bond, —NH—, —NR$^1$— (wherein $R^1$ is $C_{1-6}$ alkyl optionally having substituent(s)), —CO—, —CO$_2$—, —OCO—, —CONR$^a$— (wherein $R^a$ is a hydrogen atom or $C_{1-6}$ alkyl optionally having substituent(s), hereinafter the same), —NR$^a$CO—, —NR$^2$CONR$^3$— (wherein $R^2$ and $R^3$ are the same or different and each is a hydrogen atom or $C_{1-6}$ alkyl optionally having substituent(s), or $R^2$ and $R^3$ are optionally joined to form, together with atoms bonded thereto, a ring optionally having substituent(s)), an oxygen atom, a sulfur atom, —SO—, —SO$_2$—, —NR$^a$SO$_2$—, —SO$_2$NR$^a$—, C$_{1-6}$ alkylene optionally having substituent(s), C$_{2-6}$ alkenylene optionally having substituent(s), C$_{2-6}$ alkynylene optionally having substituent(s), —O—X$^a$— (wherein X$^a$ is C$_{1-6}$ alkylene optionally having substituent(s), hereinafter the same), —X$^a$—O—, —CO—X$^a$—, —X$^a$—CO—, —CONR$^a$—X$^a$—, —X$^a$—CONR$^a$—, —NR$^a$CO—X$^a$—, —X$^a$—NR$^a$CO—, —S—X$^a$—, —X$^a$—S—, —SO—X$^a$—, —X$^a$—SO—, —NR$^a$—X$^a$—, —X$^a$—NR$^a$—, —SO$_2$—X$^a$—, —X$^a$—SO$_2$—, —C(=N—CO$_2$—R$^1$)—, —C(=N—SO$_2$—R$^1$)—, —C(=N—SO$_2$NH$_2$)—, —C(=CH—NO$_2$)—, —C(=N—CN)— or C$_{3-8}$ cycloalkylidene optionally having substituent(s), Y is a bond, —NH—, —NR$^4$— (wherein R$^4$ is C$_{1-6}$ alkyl optionally having substituent(s), hereinafter the same), —CO—, —CO$_2$—, —OCO—, —CONR$^b$— (wherein R$^b$ is a hydrogen atom or C$_{1-6}$ alkyl optionally having substituent(s), hereinafter the same), —NR$^b$CO—, —NR$^5$CONR$^6$— (wherein R$^5$ and R$^6$ are the same or different and each is a hydrogen atom or C$_{1-6}$ alkyl optionally having substituent(s), or R$^5$ and R$^6$ are optionally joined to form, together with atoms bonded thereto, a ring optionally having substituent(s)), an oxygen atom, a sulfur atom, —SO—, —SO$_2$—, —NR$^b$SO$_2$—, —SO$_2$NR$^b$—, C$_{1-6}$ alkylene optionally having substituent(s), C$_{2-6}$ alkenylene optionally having substituent(s), C$_{2-6}$ alkynylene optionally having substituent(s), —O—X$^b$— (wherein X$^b$ is C$_{1-6}$ alkylene optionally having substituent(s), hereinafter the same), —X$^b$—O—, —CO—X$^b$—, —X$^b$—CO—, —CONR$^b$—X$^b$—, —X$^b$—CONR$^b$—, —NR$^b$CO—X$^b$—, —X$^b$—NR$^b$CO—, —S—X$^b$—, —X$^b$—S—, —SO—X$^b$—, —X$^b$—SO—, —NR$^b$—X$^b$—, —X$^b$—NR$^b$—, —SO$_2$—X$^b$—, —X$^b$—SO$_2$—, —C(=N—CO$_2$—R$^4$)—, —C(=N—SO$_2$—R$^4$)—, —C(=N—SO$_2$NH$_2$)—, —C(=CH—NO$_2$)— or —C(=N—CN)—, and is a hydrogen atom, a halogen atom, C$_{1-6}$ alkyl optionally having substituent(s), C$_{3-8}$ cycloalkyl optionally having substituent(s), aryl optionally having substituent(s), a heterocyclic group optionally having substituent(s), hydroxy, nitro, amino, cyano, C$_{1-6}$ alkoxy optionally having substituent(s), mono- or di-C$_{1-6}$ alkylamino optionally having substituent(s), C$_{1-7}$ acylamino optionally having substituent(s), sulfonylamino optionally having substituent(s), hydrazino optionally having substituent(s), guanidino optionally having substituent(s) or amidino optionally having substituent(s)], or a pharmaceutically acceptable salt thereof, in producing a therapeutic agent or prophylactic agent for an ophthalmic disease caused by ocular angiogenesis.

In a preferable embodiment of the formula (1), ring B is arylene optionally having substituent(s), or a divalent heterocyclic group optionally having substituent(s), and X is a bond, —NH—, —NR$^1$— (wherein R$^1$ is C$_{1-6}$ alkyl optionally having substituent(s)), —CO—, —CO$_2$—, —OCO—, —CONR$^a$— (wherein R$^a$ is a hydrogen atom or C$_{1-6}$alkyl optionally having substituent(s), hereinafter the same), —NR$^a$CO—, —NR$^2$CONR$^3$— (wherein R$^2$ and R$^3$ are the same or different and each is a hydrogen atom or C$_{1-6}$ alkyl optionally having substituent(s), or R$^2$ and R$^3$ are optionally joined to form, together with atoms bonded thereto, a ring optionally having substituent(s)), an oxygen atom, a sulfur atom, —SO—, —SO$_2$—, —NR$^a$SO$_2$—, —SO$_2$NR$^a$—, C$_{1-6}$ alkylene optionally having substituent(s), C$_{2-6}$ alkenylene optionally having substituent(s), C$_{2-6}$ alkynylene optionally having substituent(s), —O—X$^a$— (wherein X$^a$ is C$_{1-6}$ alkylene optionally having substituent(s), hereinafter the same), —X$^a$—O—, —CO—X$^a$—, —X$^a$—CO—, —CONR$^a$—X$^a$—, —X$^a$—CONR$^a$—, —NR$^a$CO—X$^a$—, —X$^a$—NR$^a$CO—, —S—X$^a$—, —X$^a$—S—, —SO—X$^a$—, —X$^a$—SO—, —NR$^a$—X$^a$—, —X$^a$—NR$^a$—, —SO$_2$—X$^a$—, —X$^a$—SO$_2$—, —C(=N—CO$_2$—R$^1$)—, —C(=N—SO$_2$—R$^1$)—, —C(=N—SO$_2$NH$_2$)—, —C(=CH—NO$_2$)— or —C(=N—CN)—.

In another preferable embodiment of the formula (1), m is 0 or 2.

In another preferable embodiment of the formula (1), m is 0.

In another preferable embodiment of the formula (1), X is a bond, —NH—, —NR$^1$— (wherein R$^1$ is C$_{1-6}$ alkyl optionally having substituent(s)), —CO—, —CO$_2$—, —OCO—, —CONR$^a$— (wherein R$^a$ is a hydrogen atom or C$_{1-6}$ alkyl optionally having substituent(s), hereinafter the same), —NR$^a$CO—, —NR$^2$CONR$^3$— (wherein R$^2$ and R$^3$ are the same or different and each is a hydrogen atom or C$_{1-6}$ alkyl optionally having substituent(s)), an oxygen atom, a sulfur atom, —SO—, —SO$_2$—, —NR$^a$SO$_2$—, —SO$_2$NR$^a$—, C$_{2-6}$ alkenylene optionally having substituent(s), —CO—X$^a$— (wherein X$^a$ is C$_{1-6}$ alkylene optionally having substituent(s), hereinafter the same), —X$^a$—CO—, —CONR$^a$—X$^a$—, —X$^a$—CONR$^a$—, —NR$^a$CO—X$^a$—, —X$^a$—NR$^a$CO— or C$_{3-8}$ cycloalkylidene optionally having substituent(s).

In another preferable embodiment of the formula (1), X is a bond, —CO—, —CONR$^a$— (wherein R$^a$ is a hydrogen atom or C$_{1-6}$ alkyl optionally having substituent(s), hereinafter the same), —NR$^a$CO—, —CO—X$^a$— (wherein X$^a$ is C$_{1-6}$ alkylene optionally having substituent(s), hereinafter the same), —X$^a$—CO—, —CONR$^a$—X$^a$—, —X$^a$—CONR$^a$—, —NR$^a$CO—X$^a$— or —X$^a$—NR$^a$CO—.

In another preferable embodiment of the formula (1), Y is a bond, —NH—, —NR$^4$— (wherein R$^4$ is C$_{1-6}$ alkyl optionally having substituent(s)), —CO—, —CO$_2$—, —OCO—, —CONR$^b$— (wherein R$^b$ is a hydrogen atom or C$_{1-6}$ alkyl optionally having substituent(s), hereinafter the same), —NR$^b$CO—, —NR$^5$CONR$^6$— (wherein R$^5$ and R$^6$ are the same or different and each is a hydrogen atom or C$_{1-6}$ alkyl optionally having substituent(s)), an oxygen atom, a sulfur atom, —SO—, —SO$_2$—, —NR$^b$SO$_2$—, —SO$_2$NR$^b$—, —CO—X$^b$— (wherein X$^b$ is C$_{1-6}$ alkylene optionally having substituent(s), hereinafter the same), —X$^b$—CO—, —CONR$^b$—X$^b$—, —X$^b$—CONR$^b$—, —NR$^b$CO—X$^b$— or —X$^b$—NR$^b$CO—.

In another preferable embodiment of the formula (1), Y is a bond, —CO—, —CONR$^b$— (wherein R$^b$ is a hydrogen atom or C$_{1-6}$ alkyl optionally having substituent(s), hereinafter the same), —NR$^b$CO—, —CO—X$^b$— (wherein X$^b$ is C$_{1-6}$ alkylene optionally having substituent(s), hereinafter the same), —X$^b$—CO—, —CONR$^b$—X$^b$—, —X$^b$CONR$^b$—, —NR$^b$CO—X$^b$— or —X$^b$—NR$^b$CO—.

In another preferable embodiment of the formula (1), Z is a hydrogen atom, a halogen atom, C$_{1-6}$ alkyl optionally having substituent(s), C$_{3-8}$ cycloalkyl optionally having substituent(s), aryl optionally having substituent(s), a heterocyclic group optionally having substituent(s), hydroxy, nitro, amino, cyano, C$_{1-6}$alkoxy optionally having substituent(s), mono- or di-C$_{1-6}$ alkylamino optionally having substituent(s), C$_{1-7}$ acylamino optionally having substituent(s), sulfonylamino optionally having substituent(s), hydrazino optionally having substituent(s), guanidino optionally having substituent(s), or amidino optionally having substituent(s).

In another preferable embodiment of the formula (1), Z is a hydrogen atom, hydroxy, amino, C$_{1-6}$ alkyl optionally having substituent(s), C$_{1-6}$ alkoxy optionally having substituent(s), aryl optionally having substituent(s) or a heterocyclic group optionally having substituent(s).

Another preferable embodiment of the formula (1) is the following formula (1a)

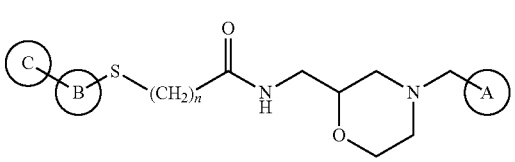

(1a)

[wherein ring C is aryl optionally having substituent(s) or heteroaryl optionally having substituent(s), and other symbols are as defined for the above-mentioned formula (1)].

In another preferable embodiment of the formula (1) or the formula (1a), ring A is phenyl optionally having substituent(s).

In another preferable embodiment of the formula (1) or the formula (1a), n is an integer of 1 to 3.

In another preferable embodiment of the formula (1) or the formula (1a), the absolute configuration of the 2-position of morpholine is the S configuration.

Another preferable embodiment of the formula (1) is selected from the group consisting of
(2S)-[4-(carboxymethyl)thiazol-2-ylthio]-N-{[4-(3,4-dichlorobenzyl)morpholin-2-yl]methyl}acetamide,
(2S)-[4-(3-aminophenyl)thiazol-2-ylthio]-N-{[4-(3,4-dichlorobenzyl)morpholin-2-yl]methyl}acetamide,
(2S)-[4-(3-carbamoyl-4-hydroxyphenyl)thiazol-2-ylthio]-N-{[4-(3,4-dichlorobenzyl)morpholin-2-yl]methyl}acetamide,
(2S)—N-{[4-(3,4-dichlorobenzyl)morpholin-2-yl]methyl}-[4-(pyridin-4-yl)thiazol-2-ylthio]acetamide,
(2S)—N-{[4-(3,4-dichlorobenzyl)morpholin-2-yl]methyl}-[4-(3,4-dimethoxyphenyl)thiazol-2-ylthio]acetamide,
(2S)-(4-carbamoylthiazol-2-ylthio)-N-{[4-(3,4-dichlorobenzyl)morpholin-2-yl]methyl}acetamide,
(2S)-{4-[(2-amino-2-oxoethyl)aminocarbonyl]thiazol-2-ylthio}-N-{[4-(3,4-dichlorobenzyl)morpholin-2-yl]methyl}acetamide,
(2S)—N-{[4-(3,4-dichlorobenzyl)morpholin-2-yl]methyl}-[4-(5-methyl-1,2,4-oxadiazol-3-yl)thiazol-2-ylthio]acetamide,
(2S)-(5-amino-8H-indeno[1,2-d]thiazol-2-ylthio)-N-{[4-(3,4-dichlorobenzyl)morpholin-2-yl]methyl}acetamide,
(2S)-(4-carboxyphenylthio)-N-{[4-(3,4-dichlorobenzyl)morpholin-2-yl]methyl}acetamide,
(2S)-{4-[(2-amino-2-oxoethyl)aminocarbonyl]phenylthio}-N-{[4-(3,4-dichlorobenzyl)morpholin-2-yl]methyl}acetamide,
(2S)-{4-[(2-carboxyethyl)aminocarbonyl]thiazol-2-ylthio}-N-{[4-(3,4-dichlorobenzyl)morpholin-2-yl]methyl}acetamide,
(2S)-(5-acetamino-1,3,4-thiadiazol-2-ylthio)-N-{[4-(3,4-dichlorobenzyl)morpholin-2-yl]methyl}acetamide,
(2S)-4-(4-carbamoylthiazol-2-ylthio)-N-{[4-(3,4-dichlorobenzyl)morpholin-2-yl]methyl}butylamide,
(2S)—N-{[4-(3,4-dichlorobenzyl)morpholin-2-yl]methyl}-[4-(1H-tetrazol-5-yl)thiazol-2-ylthio]acetamide,
(2S)—N-{[4-(3,4-dichlorobenzyl)morpholin-2-yl]methyl}-([1,3]thiazolo[5,4-b]pyridin-2-ylthio)acetamide,
(2S)-(E)-[4-(2-carbamoylethen-1-yl)thiazol-2-ylthio]-N-{[4-(3,4-dichlorobenzyl)morpholin-2-yl]methyl}acetamide,
(2S)-[4-(carbamoylmethyl)thiazol-2-ylthio]-N-{[4-(3,4-fluorobenzyl)morpholin-2-yl]methyl}acetamide,
(2S)-[4-(carbamoylmethyl)thiazol-2-ylthio]-N-{[4-(4-fluorobenzyl)morpholin-2-yl]methyl}acetamide,
(2S)-(4-carboxy-5-methylthiazol-2-ylthio)-N-{[4-(3,4-dichlorobenzyl)morpholin-2-yl]methyl}acetamide,
(2S)-(4-carbamoyl-5-methylthiazol-2-ylthio)-N-{[4-(3,4-dichlorobenzyl)morpholin-2-yl]methyl}acetamide,
(2S)-(4-carbamoylthiazol-2-ylthio)-N-{[4-(3-chloro-4-fluorobenzyl) morpholin-2-yl]methyl}acetamide,
(2S)-[4-(2-amino-2-oxoethyl)aminocarbonylthiazol-2-ylthio]-N-{[4-(3,4-difluorobenzyl)morpholin-2-yl]methyl}acetamide,
(2S)-(5-amino-1,3,4-thiadiazol-2-ylthio)-N-{[4-(3-chlorobenzyl)morpholin-2-yl]methyl}acetamide,
(2S)-(5-amino-1,3,4-thiadiazol-2-ylthio)-N-{[4-(3,4-difluorobenzyl)morpholin-2-yl]methyl}acetamide,
(2S)—N-{[4-(3,4-dichlorobenzyl)morpholin-2-yl]methyl}-(pyrimidin-2-ylthio)acetamide,
(2S)-(3-acetyl-2-oxo-2H-chromen-6-ylthio)-N-{[4-(3,4-dichlorobenzyl) morpholin-2-yl]methyl}acetamide,
(2S)—N-{[4-(3,4-difluorobenzyl)morpholin-2-yl]methyl}-(6-oxo-1,6-dihydropyridazin-3-ylthio) acetamide,
(2S)-[6-(carbamoylmethyl)pyrazin-2-ylthio]-N-{[4-(3,4-dichlorobenzyl)morpholin-2-yl]methyl}acetamide, and
(2S)-4-(cyclopentanesulfonyl)-N-{[4-(3-chloro-4-fluorobenzyl)morpholin-2-yl]methyl}butylamide, and pharmaceutically acceptable salts thereof.

Here, a preferable embodiment of the ophthalmic disease caused by ocular angiogenesis includes ophthalmic diseases caused by angiogenesis in the cornea, choroid or retina.

Another preferable embodiment of the ophthalmic disease caused by ocular angiogenesis is retinopathy of prematurity, diabetic retinopathy, corneal neovascularization, macular degeneration, neovascular glaucoma, choroidal neovascularization disease, neovascular maculopathy, branch retinal vein occlusion, central retinal vein occlusion or diabetic maculopathy.

Another preferable embodiment of the ophthalmic disease caused by ocular angiogenesis is age-related macular degeneration.

Another preferable embodiment of the ophthalmic disease caused by ocular angiogenesis is wet age-related macular degeneration.

Here, a combination of a more preferable embodiment of the formula (1) and a more preferable ophthalmic disease caused by ocular angiogenesis is a combination of (2S)-[4-(carboxymethyl)thiazol-2-ylthio]-N-{[4-(3,4-dichlorobenzyl)morpholin-2-yl]methyl}acetamide hydrobromide as the formula (1), and age-related macular degeneration as the ophthalmic disease caused by ocular angiogenesis.

Here, a combination of a particularly preferable embodiment of the formula (1) and a particularly preferable ophthalmic disease caused by ocular angiogenesis is a combination of (2S)-[4-(carboxymethyl)thiazol-2-ylthio]-N-{[4-(3,4-dichlorobenzyl)morpholin-2-yl]methyl}acetamide hydrobromide as the formula (1), and wet age-related macular degeneration as the ophthalmic disease caused by ocular angiogenesis.

Effect of the Invention

Since the compound of the present invention suppresses ocular angiogenesis, it is considered to be useful as a therapeutic agent or prophylactic agent for an ophthalmic disease caused by ocular angiogenesis, specifically retinopathy of prematurity, diabetic retinopathy, corneal neovascularization, macular degeneration, neovascular glaucoma, choroidal neovascularization, neovascular maculopathy, branch retinal vein occlusion, central retinal vein occlusion, diabetic maculopathy or the like.

BRIEF DESCRIPTION OF THE DRAWINGS

FIG. 1 is a graph showing a choroidal neovascularization-suppressive action of the compound of the present invention on a laser irradiation-induced choroidal neovascularization mouse model (CNV model).

DESCRIPTION OF EMBODIMENTS

The terms and symbols used in the present specification are defined as follows.

Examples of the "halogen atom" include fluorine atom, chlorine atom, bromine atom, iodine atom and the like.

The "aryl" of the "aryl optionally having substituent(s)" means monocyclic-tricyclic $C_{6-14}$ aryl. Examples thereof include phenyl, naphthyl, anthryl, indenyl and the like, preferable examples thereof include phenyl, naphthyl and the like, and a more preferable example thereof is phenyl.

The "aryl" may be partially hydrogenated. The position to be hydrogenated is not particularly limited. Examples of the partially hydrogenated aryl include tetrahydronaphthyl, indanyl and the like.

When "aryl" has a "substituent", the kind and number thereof are not particularly limited, and 1 to 4 substituents selected from the "substituent" defined below is/are present at substitutable position(s) thereof. Preferable examples of the substituent that aryl optionally has include a halogen atom, cyano, nitro, $C_{1-6}$ alkyl, $C_{1-6}$ haloalkyl, $C_{1-6}$ alkoxy, hydroxy, amino, mono- or di-($C_{1-11}$ acyl)amino, carboxy, $C_{1-6}$alkoxy-carbonyl, carbamoyl, hydroxyamidino and the like, more preferable examples thereof include chlorine atom, fluorine atom, cyano, nitro, methyl, trifluoromethyl, methoxy, hydroxy, amino, acetylamino, carboxy, methoxy-carbonyl, carbamoyl, hydroxyamidino, more preferable examples thereof include fluorine atom, chlorine atom, methyl and trifluoromethyl, further more preferable examples thereof include fluorine atom and chlorine atom.

The "heteroaryl" of the "heteroaryl optionally having substituent(s)" means a 5- to 7-membered aromatic heterocyclic (monocyclic) group containing, as a ring atom other than carbon atom, 1 to 3 kinds of 1 to 4 hetero atoms selected from a nitrogen atom, a sulfur atom and an oxygen atom, and examples thereof include furyl, thienyl, pyrrolyl, thiazolyl, pyrazolyl, oxazolyl, isoxazolyl, isothiazolyl, imidazolyl, 1,2,4-oxadiazolyl, 1,3,4-oxadiazolyl, 1,2,3-triazolyl, 1,2,4-triazolyl, 1,2,4-thiadiazolyl, 1,3,4-thiadiazolyl, tetrazolyl, pyridyl, pyrimidinyl, pyrazinyl, pyridazinyl, 1,3,5-triazinyl, azepinyl, diazepinyl and the like. In addition, "heteroaryl" includes a group induced from an aromatic heterocycle (bicyclic or more) wherein 5- to 7-membered aromatic heterocycle containing, as a ring atom other than carbon atom, 1 to 3 kinds of 1 to 4 hetero atoms selected from a nitrogen atom, a sulfur atom and an oxygen atom is fused with a benzene ring or the above-mentioned aromatic heterocyclic (monocyclic) group, and examples thereof include indolyl, isoindolyl, benzo[b]furyl, benzo[b]thienyl, benzimidazolyl, benzoxazolyl, benzisoxazolyl, benzothiazolyl, benzisothiazolyl, quinolyl, isoquinolyl and the like.

The "heteroaryl" may be partially hydrogenated. The position to be hydrogenated is not particularly limited. Examples of the partially hydrogenated heteroaryl include tetrahydrobenzoimidazolyl, tetrahydroquinolyl, tetrahydroisoquinolyl and the like.

Preferable examples of heteroaryl include furyl, thienyl, thiazolyl, pyridyl, indolyl, benzo[b]furyl, benzo[b]thienyl, benzoxazolyl, benzothiazolyl, quinolyl, and isoquinolyl, and more preferable examples thereof include furyl, thienyl, thiazolyl, and pyridyl.

When "heteroaryl" has a "substituent", the kind and number thereof are not particularly limited, and 1 to 4 substituents selected from the "substituents" defined below is/are present at substitutable position(s). Preferable examples of the substituent that heteroaryl optionally has include a halogen atom, cyano, and nitro, and a more preferable example thereof is a halogen atom.

The "arylene" of the "arylene optionally having substituent(s)" means a divalent group further having a bond at any position of the above-mentioned "aryl", and examples thereof include divalent groups such as phenylene, naphthylene, indenylene and the like.

The "arylene" may be partially hydrogenated. The position to be hydrogenated is not particularly limited. Examples of the partially hydrogenated arylene include tetrahydronaphthylene, indanylene and the like.

Preferable examples of arylene include phenylene, naphthylene, indanylene and the like, and more preferable examples thereof include phenylene and the like.

When "arylene" has a "substituent", the kind and number thereof are not particularly limited, and 1 to 3 substituents selected from the "substituents" defined below is/are present at substitutable position(s). Preferable examples of the substituent that arylene optionally has include $C_{1-6}$ alkyl, $C_{1-6}$ alkoxy, hydroxy, oxo and the like, and a more preferable example thereof is oxo.

The "heterocyclic group" of the "divalent heterocyclic group optionally having substituent(s)" for ring B and the "heterocyclic group optionally having substituent(s)" for Z means a 5- to 14-membered monocyclic-tricyclic heterocyclic group containing, as a ring atom other than carbon atom, 1-3 kinds of 1-4 hetero atoms selected from a nitrogen atom, a sulfur atom and an oxygen atom. The "heterocyclic group" encompasses a saturated ring, an aromatic ring (encompassing "heteroaryl" defined above), and partially hydrogenated ring groups thereof. Examples of the partially hydrogenated heteroaryl include dihydrofuryl, dihydrothienyl, pyrrolinyl, thiazolinyl, pyrazolinyl, oxazolinyl, isoxazolinyl, isothiazolinyl, imidazolinyl, 1,2,4-oxadiazolinyl, 1,3,4-oxadiazolinyl, 1,2,3-triazolinyl, 1,2,4-triazolinyl, 1,2,4-thiadiazolinyl, 1,3,4-thiadiazolinyl, dihydropyridazinyl, tetrahydrobenzoimidazolyl, tetrahydroquinolyl, tetrahydroisoquinolyl and the like.

Examples of the "saturated heterocyclic group" include pyrrolidyl, piperidyl, piperazinyl, tetrahydrofuranyl, morpholinyl, thiazolidyl, thiomorpholinyl, homopiperazinyl and the like. The "heterocyclic group" encompasses a crosslinked heterocyclic group containing, as a ring atom other than carbon atom, 1-4 hetero atoms selected from an oxygen atom, a sulfur atom and a nitrogen atom, and examples of the crosslinked ring group include 3-azabicyclo[3.2.2]nonan-3-yl, 8-azabicyclo[3.2.1]octan-8-yl and the like.

When "heterocyclic group" has a "substituent", the kind and number thereof are not particularly limited, and 1 to 4 substituents selected from the "substituent" defined below is/are present at substitutable position(s) thereof. Preferable examples of the substituent that the heterocyclic group optionally has include $C_{1-6}$alkyl, hydroxy, nitro, amino, cyano, carboxy, $C_{1-6}$ alkoxy-carbonyl, carbamoyl, oxo and the like, and methyl, ethoxycarbonyl, carbamoyl, and oxo are more preferable.

Preferable examples of the "heterocyclic group" include pyridyl, pyrazinyl, pyrimidinyl, pyridazinyl, imidazolyl, pyrrolyl, pyrrolidyl, morpholinyl, thienyl, furyl, thiazolyl, pyrazolyl, isothiazolyl, oxazolyl, isoxazolyl, quinolyl, isoquinolyl, tetrahydroquinolyl, tetrahydroisoquinolyl, quinolizinyl, quinazolyl, quinoxalinyl, cinnolinyl, phthalazinyl, 1,8-naphthyridinyl, acrydinyl, purinyl, pteridinyl, 1,2,4-oxadiazolyl, 1,2,4-oxadiazolinyl, 1,3,4-oxadiazolyl, 1,2,3-triazolyl, 1,2,4-triazolyl, 1,3,5-triazinyl, 1,2,4-thiadiazolyl, 1,3,4-thiadiazolyl, tetrazolyl, piperidyl, piperazinyl, azepinyl, azepanyl, diazepanyl, diazepinyl, tetrahydrofuranyl, morpholinyl, indolyl, isoindolyl, indolinyl, isoindolinyl, indazolyl, indolizinyl, carbazolyl, tetrahydrobenzimidazolyl, chromanyl, isochromanyl, chromenyl, isochromenyl, [1,3]thiazolo[5,4-b]pyridyl, 4,5,6,7-tetrahydro[1,3]thiazolo[5,4-c]pyridyl, 1H-benzo[b]azepinyl, 2,3-dihydro-1H-benzo[b]azepinyl, thieno[3,2-c]pyridyl, 3-azabicyclo[3.2.2]nonan-3-yl, 8-azabicyclo[3.2.1]octan-8-yl, benzo[b]furyl, benzo[b]thienyl, benzimidazolyl, benzoxazolyl, benzisoxazolyl, benzothiazolyl, benzisothiazolyl, 8H-indeno[1,2-d]thiazolyl, 4,5-dihydro-naphtho[1,2-d]thiazolyl and the like, more preferable examples thereof include pyridyl, pyrazinyl, pyrimidinyl, pyridazinyl, thienyl, furyl, thiazolyl, pyrazolyl, isothiazolyl, oxazolyl, isoxazolyl, 1,2,4-oxadiazolyl, 1,3,4-oxadiazolyl, 1,2,3-triazolyl, 1,2,4-triazolyl, 1,3,5-triazinyl, 1,2,4-thiadiazolyl, 1,3,4-thiadiazolyl, benzo[b]furyl, benzo[b]thienyl, benzimidazolyl, benzoxazolyl, benzisoxazolyl, benzothiazolyl, benzisothiazolyl, 8H-indeno[1,2-d]thiazolyl, and 4,5-dihydro-naphtho[1,2-d]thiazolyl, still more preferable examples thereof include thiazolyl, 1,3,4-thiadiazolyl, pyridyl, pyrimidinyl, pyridazinyl, pyrazinyl, thienyl can be mentioned, and further more preferable examples thereof include thiazolyl, 1,3,4-thiadiazolyl, pyridazinyl, and pyrazinyl.

The "divalent heterocyclic group optionally having substituent(s)" means a divalent group having a bond at any position of the above-mentioned "heterocyclic group". The position of the bond is not particularly limited, and can be appropriately selected according to the kind of the group. Preferable examples of the "divalent heterocyclic group" include pyrrolyl, thienyl, furyl, thiazolyl, pyrazolyl, isothiazolyl, oxazolyl, isoxazolyl, 1,2,4-oxadiazolyl, 1,3,4-oxadiazolyl, 1,2,4-triazolyl, 1,2,4-thiadiazolyl, 1,3,4-thiadiazolyl, pyridyl, pyrazinyl, pyrimidinyl, optionally partially hydrogenated pyridazinyl, optionally partially hydrogenated indenothiazolyl, optionally partially hydrogenated naphtothiazolyl, quinazolyl, chromenyl, optionally partially hydrogenated thiazolopyridyl, benzoazepinyl, thienopyridyl, benzothiazolyl, imidazolyl, tetrazolyl and the like, more preferable examples thereof include thienyl, thiazolyl, 1,3,4-thiadiazolyl, pyridyl, pyrimidinyl, pyridazinyl, pyrazinyl and the like, and still more preferable examples thereof include thiazolyl, 1,3,4-thiadiazolyl, pyridazinyl, and pyrazinyl.

When "a divalent heterocyclic group" has a "substituent", the kind and number thereof are not particularly limited, and 1 to 3 substituents selected from the "substituent" defined below is/are present at substitutable position(s) thereof. Preferable examples of the substituent that the divalent heterocyclic group optionally has include $C_{1-6}$ alkyl, $C_{1-6}$ haloalkyl, $C_{1-6}$ alkoxy, hydroxy, a halogen atom, oxo, thioxo and the like, more preferable examples thereof include methyl and oxo, and oxo is still more preferable.

The "$C_{3-8}$ cycloalkylene" of the "$C_{3-8}$ cycloalkylene optionally having substituent(s)" means $C_{3-8}$ monocyclic-tricyclic cycloalkylene (including "crosslinked cycloalkylene"), such as cyclopropylene, cyclobutylene, cyclopentylene, cyclohexylene, cycloheptylene, cyclooctylene, norbornylene, bicyclo[2.2.1]heptylene, bicyclo[2.2.2]octylene and the like, preferably cyclopropylene, cyclobutylene, cyclopentylene and cyclohexylene.

When "$C_{3-8}$ cycloalkylene" has a "substituent", the kind and number thereof are not particularly limited, and 1 to 4 substituents selected from the "substituent" defined below is/are present at substitutable position(s) thereof. Preferable examples of the substituent that the $C_{3-8}$ cycloalkylene optionally has include $C_{1-6}$alkyl, $C_{1-6}$ alkoxy, hydroxy, amino, a halogen atom, $C_{1-6}$ haloalkyl, $C_{1-6}$ haloalkoxy and the like.

The "$C_{1-6}$ alkyl" of the "$C_{1-6}$alkyl optionally having substituent(s)" means $C_{1-6}$ straight chain or branched chain alkyl, such as methyl, ethyl, n-propyl, isopropyl, n-butyl, isobutyl, secondary butyl, tertiary butyl, pentyl, isopentyl, neopentyl, tertiary pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl and the like.

Preferable examples of the "$C_{1-6}$ alkyl" include methyl, ethyl, n-propyl, isopropyl, n-butyl, isobutyl and the like, and more preferable examples include methyl, ethyl and the like.

When "$C_{1-6}$ alkyl" has a "substituent", the kind and number thereof are not particularly limited, and 1 to 4 substituents selected from the "substituent" defined below is/are present at substitutable position(s) thereof, and the kind and number thereof are not particularly limited. Preferable examples of the substituent that the "$C_{1-6}$ alkyl" optionally has include $C_{1-6}$ alkoxy, hydroxy, a halogen atom and the like.

Examples of the "ring" of —NR$^2$CONR$^3$— (wherein R$^2$ and R$^3$ are the same or different and each is a hydrogen atom or alkyl, or R$^2$ and R$^3$ are optionally joined to form a ring together with atoms bonded thereto) for X include a "nitrogen-containing saturated heterocycle" (e.g., 1,3-imidazolidin-2-one, 3,4,5,6-tetrahydro-2(1H)-pyrimidinone and the like) included in the "heterocyclic group" defined above.

When the "ring" has a "substituent", the kind and number thereof are not particularly limited, and 1 to 3 substituents selected from the "substituent" defined below is/are present at substitutable position(s) thereof. Preferable examples of the substituent that the "ring" optionally has include $C_{1-6}$ alkyl, $C_{1-6}$ alkoxy, hydroxy, a halogen atom and the like.

The "$C_{1-6}$ alkylene" of the "$C_{1-6}$ alkylene optionally having substituent(s)" means an alkylene chain having 1-6 carbon atoms, such as methylene, ethylene, trimethylene, tetramethylene, pentamethylene, hexamethylene and the like. Preferable examples of the "$C_{1-6}$ alkylene" include methylene, ethylene and trimethylene, and more preferable examples thereof include methylene and ethylene.

When "$C_{1-6}$ alkylene" has a "substituent", the kind and number thereof are not particularly limited, and 1 to 3 substituents selected from the "substituent" defined below is/are present at substitutable position(s). Preferable examples of the substituent that the "$C_{1-6}$ alkylene" optionally has include $C_{1-6}$ alkyl, $C_{1-6}$ alkoxy, hydroxy, carboxy, carbamoyl and the like, and methyl, isobutyl and carboxy are more preferable.

When "$C_{1-6}$ alkylene" is substituted by one or more $C_{1-6}$ alkyl mentioned above, it shows a branched alkylene chain (e.g., methylmethylene, dimethylmethylene, 1-methylethylene, 2-methylethylene, 1,1-dimethylethylene, 2,2-dimethylethylene, ethylmethylene, diethylmethylene, 1-ethylethylene, 2-ethylethylene, 1-methyltrimethylene, 1,1-dimethyltrimethylene, 2-methyltrimethylene, 2,2-dimethyltrimethylene, 3-methyltrimethylene, 3,3-dimethyltrimethylene, 1-ethyltrimethylene, 2-ethyltrimethylene, 3-ethyltrimethylene and the like).

The "$C_{2-6}$ alkenylene" of the "$C_{2-6}$ alkenylene optionally having substituent(s)" is $C_{2-6}$ straight chain or branched chain alkenylene having a double bond at any position of the above-mentioned "$C_{1-6}$ alkylene". The position and number of the double bond are not particularly limited. Examples of the "$C_{2-6}$ alkenylene" include vinylene, 1-propenylene, 2-propenylene, 1-butenylene, 2-butenylene, 3-butenylene, 1-pentenylene and the like can be mentioned, preferably, vinylene, 1-propenylene, and 2-propenylene. When "$C_{2-6}$ alkenylene" has a "substituent", the kind and number thereof are not particularly limited, and 1 to 3 substituents selected from the "substituent" defined below is/are present at substitutable position(s). Preferable examples of the substituent that the "$C_{2-6}$ alkenylene" optionally has include $C_{1-6}$ alkyl, $C_{1-6}$ alkoxy, hydroxy, a halogen atom and the like.

The "$C_{2-6}$ alkynylene" of the "$C_{2-6}$ alkynylene optionally having substituent(s)" is $C_{2-6}$ straight chain or branched chain alkynylene having a triple bond at any position of the above-mentioned "$C_{1-6}$ alkylene". The position and number of the triple bond are not particularly limited. Examples of the "$C_{2-6}$ alkynylene" include ethynylene, 1-propynylene, 2-propynylene, 1-butynylene, 2-butynylene, 3-butynylene, 1-pentynylene and the like can be mentioned, preferably, ethynylene, 1-propynylene, and 2-propynylene. When "$C_{2-6}$ alkynylene" has a "substituent", the kind and number thereof are not particularly limited, and 1 to 3 substituents selected from the "substituent" defined below is/are present at substitutable position(s). Preferable examples of the substituent that the "$C_{2-6}$ alkynylene" optionally has include $C_{1-6}$alkyl, $C_{1-6}$ alkoxy, hydroxy, a halogen atom and the like.

The "$C_{3-8}$cycloalkylidene" of the "$C_{3-8}$ cycloalkylidene optionally having substituent(s)" means $C_{3-8}$ monocyclic-tricyclic cycloalkylidene (including "crosslinked cycloalkylidene"), and examples thereof include cyclopropylidene, cyclobutylidene, cyclopentylidene, cyclohexylidene, cycloheptylidene, cyclooctylidene, norbornylidene, bicyclo[2.2.1]heptylidene, bicyclo[2.2.2]octylidene and the like, and cyclopropylidene, cyclobutylidene, cyclopentylidene and cyclohexylidene are preferable.

When "$C_{3-8}$ cycloalkylidene" has a "substituent", the kind and number thereof are not particularly limited, and 1 to 4 substituents selected from the "substituent" defined below is/are present at substitutable position(s) thereof. Preferable examples of the substituent that $C_{3-8}$ cycloalkylidene optionally has include $C_{1-6}$alkyl, $C_{1-6}$ alkoxy, hydroxy, amino, a halogen atom, $C_{1-6}$ haloalkyl, $C_{1-6}$ haloalkoxy and the like.

Examples of the "ring" of —NR$^5$CONR$^6$— (wherein R$^5$ and R$^6$ are the same or different and each is a hydrogen atom or alkyl, or R$^5$ and R$^6$ are optionally joined to form a ring together with atoms bonded thereto) for Y include a "nitrogen-containing saturated heterocycle" (e.g., 1,3-imidazolidin-2-one, 3,4,5,6-tetrahydro-2(1H)-pyrimidinone and the like) included in the "heterocyclic group" defined above.

When the "ring" has a "substituent", the kind and number thereof are not particularly limited, and 1 to 3 substituents selected from the "substituent" defined below is/are present at substitutable position(s) thereof. Preferable examples of the substituent that the "ring" optionally has include $C_{1-6}$ alkyl, $C_{1-6}$ alkoxy, hydroxy, a halogen atom and the like.

The "$C_{3-8}$ cycloalkyl" of the "$C_{3-8}$ cycloalkyl optionally having substituent(s)" means $C_{3-8}$ monocyclic-tricyclic cycloalkyl (including "crosslinked cycloalkyl"), and examples thereof include cyclopropyl, cyclobutyl, cyclopentyl, cyclohexyl, cycloheptyl, cyclooctyl, norbornyl, bicyclo[2.2.1]heptyl or bicyclo[2.2.2]octyl and the like, and cyclopropyl, cyclobutyl, cyclopentyl and cyclohexyl are preferable.

When "$C_{3-8}$ cycloalkyl" has a "substituent", the kind and number thereof are not particularly limited, and 1 to 4 substituents selected from the "substituent" defined below is/are present at substitutable position(s) thereof. Preferable examples of the substituent that $C_{3-8}$ cycloalkyl optionally has include $C_{1-6}$ alkyl, $C_{1-6}$ alkoxy, hydroxy, a halogen atom and the like.

The "$C_{1-6}$ alkoxy" of the "$C_{1-6}$ alkoxy optionally having substituent(s)" means a $C_{1-6}$ straight chain or branched chain alkoxy, and examples thereof include methoxy, ethoxy, n-propoxy, isopropoxy, n-butoxy, isobutoxy, secondary butoxy, tertiary butoxy, pentoxy, isopentoxy, neopentoxy, tertiary pentoxy, 1-methylbutoxy, 2-methylbutoxy, 1,2-dimethylpropoxy, 1-ethylpropoxy, hexyloxy, isohexyloxy, 1-methylpentoxy, 2-methylpentoxy, 3-methylpentoxy, 1,1-dimethylbutoxy, 1,2-dimethylbutoxy, 2,2-dimethylbutoxy, 1-ethylbutoxy, 1,1,2-trimethylpropoxy, 1,2,2-trimethylpropoxy, 1-ethyl-2-methylpropoxy, 1-ethyl-1-methylpropoxy and the like.

Preferable examples of "$C_{1-6}$alkoxy" include methoxy, ethoxy, n-propoxy, isopropoxy, n-butoxy and the like, and more preferable examples thereof include methoxy, ethoxy and the like.

When "$C_{1-6}$ alkoxy" has a "substituent", the kind and number thereof are not particularly limited, and 1 to 4 substituents selected from the "substituent" defined below is/are present at substitutable position(s) thereof. The kind and number of the substituent are not particularly limited. Preferable examples of the substituent that "$C_{1-6}$ alkoxy" optionally has include $C_{1-6}$ alkyl, $C_{1-6}$ alkoxy, hydroxy, a halogen atom and the like.

The "mono- or di-$C_{1-6}$ alkylamino" of the "mono- or di-$C_{1-6}$ alkylamino optionally having substituent(s)" is alkylamino mono- or di-substituted by $C_{1-6}$ straight chain or branched chain alkyl (total carbon number of dialkylamino is 2-12), which is methylamino, dimethylamino, ethylamino, diethylamino, methylethylamino, propylamino, dipropylamino, isopropylamino, diisopropylamino, butylamino, dibutylamino, isobutylamino, secondary butylamino, tertiary butylamino, pentylamino, hexylamino or the like.

Preferable examples of "mono- or di-$C_{1-6}$ alkylamino" include methylamino, dimethylamino, ethylamino, diethylamino, methylethylamino, propylamino, dipropylamino, isopropylamino, diisopropylamino and the like, and more preferable examples thereof include methylamino, dimethylamino, ethylamino, diethylamino, methylethylamino, propylamino and the like.

When "mono- or di-$C_{1-6}$ alkylamino" has a "substituent", the kind and number thereof are not particularly limited, and 1 to 4 substituents selected from the "substituent" defined below is/are present at substitutable position(s) thereof. Preferable examples of the substituent that mono- or di-$C_{1-6}$ alkylamino optionally has include $C_{1-6}$ alkyl, $C_{1-6}$ alkoxy, hydroxy, a halogen atom and the like.

The "$C_{1-7}$ acylamino" of the "$C_{1-7}$ acylamino optionally having substituent(s)" is acylamino having $C_{1-7}$ alkanoyl (e.g., formyl, acetyl, propionyl, butyryl, valeryl, pivaloyl etc.), $C_{3-7}$ alkenoyl (e.g., acryloyl, methacryloyl, crotonoyl etc.), $C_{3-7}$ alkynoyl (e.g., propioloyl etc.), benzoyl and the like at the acyl moiety, which is acetylamino, propionylamino, butyrylamino, valerylamino, pivaloylamino, benzoylamino or the like.

Preferable examples of "$C_{1-7}$ acylamino" include acetylamino, propionylamino, butyrylamino, valerylamino, pivaloylamino, benzoylamino and the like, and more preferable examples thereof include acetylamino, propionylamino, benzoylamino and the like.

When "$C_{1-7}$ acylamino" has a "substituent", the kind and number thereof are not particularly limited, and 1 to 4 substituents selected from the "substituent" defined below is/are present at substitutable position(s) thereof. Preferable examples of the substituent that $C_{1-7}$ acylamino optionally has include $C_{1-6}$ alkyl, $C_{1-6}$ alkoxy, hydroxy, a halogen atom and the like.

When "sulfonylamino optionally having substituent(s)" has a "substituent", the kind and number thereof are not particularly limited, and a substituent selected from the "substituent" defined below is present at the amino group. Preferable examples of the substituent that sulfonylamino optionally has include amino, $C_{1-6}$ alkyl, aryl, heteroaryl and the like.

When "hydrazino optionally having substituent(s)" has a "substituent", the kind and number thereof are not particularly limited, and 1 to 3 substituents selected from the "substituent" defined below is/are present at substitutable position(s) thereof. Preferable examples of the substituent that hydrazino optionally has include $C_{1-6}$ alkyl, aryl, heteroaryl and the like. Examples of aryl and heteroaryl include those mentioned above.

When "guanidino optionally having substituent(s)" has a "substituent", the kind and number thereof are not particularly limited, and 1 to 3 substituents selected from the "substituent" defined below is/are present at substitutable position(s) thereof. Preferable examples of the substituent that guanidino optionally has include hydroxy, nitro, cyano and the like.

When "amidino optionally having substituent(s)" has a "substituent", the kind and number thereof are not particularly limited, and 1 to 3 substituents selected from the "substituent" defined below is/are present at substitutable position(s) thereof. Preferable examples of the substituent that amidino optionally has include hydroxy, nitro, cyano and the like.

The "substituent" of the above-mentioned each group optionally having substituent(s) is not particularly limited, and examples thereof include halogen atoms (e.g., fluorine atom, chlorine atom, bromine atom, iodine atom etc.), $C_{1-6}$ alkyl (e.g., $C_{1-6}$ straight chain or branched chain alkyl groups such as methyl, ethyl, n-propyl, isopropyl, n-butyl, isobutyl, secondary butyl, tertiary butyl, pentyl, isopentyl, neopentyl, tertiary pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl and the like), $C_{3-8}$ cycloalkyl (e.g., cyclopropyl, cyclobutyl, cyclopentyl, cyclohexyl, cycloheptyl, cyclooctyl, norbornyl, bicyclo[2.2.1]heptyl, bicyclo[2.2.2]octyl etc.), $C_{3-8}$ cycloalkyloxy (e.g., cyclopropyloxy, cyclobutyloxy, cyclopentyloxy, cyclohexyloxy, cycloheptyloxy, cyclooctyloxy, norbornyloxy, bicyclo[2.2.1]heptyloxy, bicyclo[2.2.2]octyloxy etc.), $C_{1-6}$ haloalkyl (e.g., the above-mentioned $C_{1-6}$ alkyl having at least one of the above-mentioned halogen atoms such as trifluoromethyl and the like), $C_{1-6}$ alkoxy (e.g., $C_{1-6}$ straight chain or branched chain alkoxy such as methoxy, ethoxy, n-propoxy, isopropoxy, n-butoxy, isobutoxy, secondary butoxy, tertiary butoxy, pentoxy, isopentoxy, neopentoxy, tertiary pentoxy, 1-methylbutoxy, 2-methylbutoxy, 1,2-dimethylpropoxy, 1-ethylpropoxy, hexyloxy, isohexyloxy, 1-methylpentoxy, 2-methylpentoxy, 3-methylpentoxy, 1,1-dimethylbutoxy, 1,2-dimethylbutoxy, 2,2-dimethylbutoxy, 1-ethylbutoxy, 1,1,2-trimethylpropoxy, 1,2,2-trimethylpropoxy, 1-ethyl-2-methylpropoxy, 1-ethyl-1-methylpropoxy and the like), $C_{1-6}$ haloalkoxy (e.g., the above-mentioned $C_{1-6}$ alkoxy having at least one of the above-mentioned halogen atoms such as trifluoromethoxy and the like), $C_{6-14}$ aryl (e.g., phenyl, naphthyl, anthryl etc.), $C_6$-14 aryloxy (e.g., phenyloxy, naphthyloxy, anthryloxy etc.), hydroxy, nitro, amino, mono- or di-$C_{1-6}$ alkylamino (e.g., methylamino, ethylamino, dimethylamino, diethylamino, propylamino, isopropylamino, butylamino, diisopropylamino etc.), mono- or di($C_{3-8}$cycloalkyl)amino (e.g., cyclopropylamino, cyclobutylamino, cyclopentylamino, cyclohexylamino, cycloheptylamino, cyclooctylamino, norbornylamino, bicyclo[2.2.1]heptylamino, bicyclo[2.2.2]octylamino, dicyclopropylamino, dicyclobutylamino, dicyclopentylamino, dicyclohexylamino, dicycloheptylamino, dicyclooctylamino, dinorbornylamino, di(bicyclo[2.2.1]heptyl)amino, di(bicyclo[2.2.2]octyl)amino etc.), mono- or di-($C_{6-14}$ aryl)amino (e.g., phenylamino, naphthylamino, anthrylamino, diphenylamino etc.), $C_{1-11}$ acyl [for example, $C_{1-7}$ alkanoyl (e.g., formyl, acetyl, propionyl, butyryl, isobutyryl, valeryl, isovaleryl, pivaloyl etc.), $C_{3-7}$ alkenoyl (e.g., acryloyl, methacryloyl, crotonoyl etc.), $C_{3-7}$ alkynoyl (e.g., propioloyl etc.), $C_{7-11}$ aroyl (e.g., benzoyl, 1-naphthoyl, 2-naphthoyl etc.) and the like], mono- or di-($C_{1-11}$ acyl) amino (e.g., amino having the above-mentioned $C_{1-11}$ acyl such as acetylamino, benzoylamino and the like), mono- or di-($C_{1-6}$ alkoxy-carbonyl)amino (e.g., methoxycarbonylamino, ethoxycarbonylamino etc.), sulfonylamino, amino-$C_{1-6}$ alkyl (e.g., aminomethyl, aminoethyl etc.), mono- or di-($C_{1-6}$ alkyl)amino-$C_{1-6}$ alkyl (e.g., methylaminomethyl, ethylaminomethyl etc.), $C_{3-8}$ cyclic amino (e.g., aziridino, azetidino, pyrrolidino, piperidino etc.), hydrazino, guanidino, amidino, hydroxyamidino, $C_{1-6}$ alkoxyamidino (e.g., methoxyamidino, ethoxyamidino etc.), aminomethylenamino, imino, carboxy, $C_{1-6}$alkoxy-carbonyl (e.g., methoxycarbonyl, ethoxycarbonyl, propoxycarbonyl, isopropoxycarbonyl, butoxycarbonyl, isobutoxycarbonyl, tertiary butoxycarbonyl, pentyloxycarbonyl etc.), carbamoyl, mono- or di-($C_{1-6}$ alkyl)aminocarbonyl (e.g., methylaminocarbonyl, ethylaminocarbonyl, propylaminocarbonyl, isopropylaminocarbonyl, butylaminocarbonyl, secondary butylaminocarbonyl, tertiary butylaminocarbonyl, dimethylaminocarbonyl, diethylaminocarbonyl, ethylmethylaminocarbonyl, dipropylaminocarbonyl, methylpropylaminocarbonyl, diisopropylaminocarbonyl etc.), mono- or di-($C_{6-14}$ aryl)aminocarbonyl (e.g., phenylaminocarbonyl, naphthylaminocarbonyl etc.), cyano, $C_{7-13}$ aralkyl (e.g., $C_{1-3}$ alkyl having $C_{6-10}$ aryl such as benzyl, 1-phenylethyl, 2-phenylethyl, 1-phenylpropyl, 3-phenylpropyl, 1-phenylbutyl, 4-phenylbutyl, 1-naphthylmethyl, 2-naphthylmethyl, 1-(1-naphthyl)ethyl, 2-(1-naphthyl)ethyl, 1-(2-naphthyl)ethyl, 2-(2-naphthyl)ethyl and the like), mono- or di-($C_{7-13}$ aralkyl)aminocarbonyl (e.g., benzylaminocarbonyl, 2-phenylethylaminocarbonyl etc.), heteroaryl (e.g., pyrrolyl, furyl, thienyl, imidazolyl, pyrazolyl, thiazolyl, isothiazolyl, oxazolyl, isoxazolyl, triazolyl, oxadiazolyl, thiadiazolyl, pyridyl, pyrazinyl, pyrimidinyl, pyridazinyl, azepinyl, diazepinyl etc.), heteroaryl-$C_{1-3}$ alkyl (e.g., the above-mentioned $C_{1-3}$ alkyl having the above-mentioned heteroaryl such as 2-pyridylmethyl, 3-pyridylmethyl, 4-pyridylmethyl, 1-(2- pyridyl)ethyl, 1-(3-pyridyl)ethyl, 1-(4-pyridyl)ethyl, 2-(2-pyridyl)ethyl, 2-(3-pyridyl)ethyl, 2-(4-pyridyl)ethyl, 3-(2-pyridyl)propyl and the like), mono- or di-(heteroaryl-$C_{1-3}$ alkyl)aminocarbonyl (e.g., 2-pyridylmethylaminocarbonyl, 3-pyridylmethylaminocarbonyl etc.), hydroxy, mercapto, $C_{1-6}$ alkylthio (e.g., methylthio, ethylthio etc.), $C_{6-14}$ arylthio (e.g., phenylthio, naphthylthio etc.), —$SO_3H$, —$SO_2NH_2$, sulfonamide, oxo or thioxo and the like.

In the formula (1), ring A is aryl optionally having substituent(s), or heteroaryl optionally having substituent(s), preferably phenyl optionally having substituent(s).

The substituent of ring A is preferably a halogen atom (e.g., fluorine atom, chlorine atom etc., particularly chlorine atom), $C_{1-6}$ alkyl optionally having substituent(s) (e.g., $C_{1-6}$ alkyl optionally substituted by a halogen atom, particularly methyl, trifluoromethyl) or $C_{1-6}$ alkoxy optionally having substituent(s) (e.g., $C_{1-6}$ alkoxy optionally substituted by a halogen atom, particularly methoxy) and the like.

Ring A is more preferably, phenyl substituted by 1 or 2 fluorine atoms or chlorine atoms, more preferably phenyl wherein the 3-position and/or the 4-position are/is substituted by 1 or 2 fluorine atoms or chlorine atoms, particularly preferably 3,4-dichlorophenyl or 3,4-difluorophenyl.

Ring B is arylene optionally having substituent(s), a divalent heterocyclic group optionally having substituent(s), or $C_{3-8}$ cycloalkylene optionally having substituent(s), preferably arylene optionally having substituent(s), or heteroarylene optionally having substituent(s). Preferable examples of ring B include phenylene, thienylene, pyridylene, thiazolylene optionally substituted by methyl, 1,3,4-thiadiazolylene, pyridazinylene which is optionally substituted by oxo and optionally partially hydrogenated, indenothiazolylene, naphthothiazolylene, thiazolopyridylene, benzothiazolylene, optionally partially hydrogenated thiazolopyridylene, isoxazolylene, pyrimidinylene, chromenylene optionally substituted by oxo, quinazolinylene, benzazepinylylene, thienopyridylene, indanylene optionally substituted by oxo, furylene, naphthylene, imidazolylene, pyrazinylene, cyclopentylene, and tetrazolylene, and more preferred are phenylene, thienylene, thiazolylene, 1,3,4-thiadiazolylene, and pyridazinylene which is optionally substituted by oxo and optionally partially hydrogenated. A furthermore preferable embodiment is thiazolylene. A still more preferable another embodiment is 1,3,4-thiadiazolylene. Another furthermore preferable embodiment is pyridazinylene which is optionally substituted by oxo and optionally partially hydrogenated. The substituent of ring B is preferably $C_{1-6}$ alkyl, oxo or the like, and methyl is more preferable.

Said m is an integer of 0 to 2, preferably 0 or 2, more preferably 0.

Said n is an integer of 1 to 5, preferably 1 to 3, more preferably 1.

X is a bond, —NH—, —$NR^1$— (wherein $R^1$ is $C_{1-6}$ alkyl optionally having substituent(s), hereinafter the same), —CO—, —$CO_2$—, —OCO—, —$CONR^a$— (wherein $R^a$ is a hydrogen atom or $C_{1-6}$ alkyl optionally having substituent(s), hereinafter the same), —$NR^aCO$—, —$NR^2CONR^3$— (wherein $R^2$ and $R^3$ are the same or different and each is a hydrogen atom or $C_{1-6}$ alkyl optionally having substituent(s), or $R^2$ and $R^3$ are optionally joined to form, together with atoms bonded thereto, a ring optionally having substituent(s), hereinafter the same), an oxygen atom, a sulfur atom, —SO—, —$SO_2$—, —$NR^aSO_2$—, —$SO_2NR^a$—, $C_{1-6}$ alkylene optionally having substituent(s), $C_{2-6}$ alkenylene optionally having substituent(s), $C_{2-6}$ alkynylene optionally having substituent(s), —O—$X^a$— (wherein $X^a$ is $C_{1-6}$ alkylene optionally having substituent(s), hereinafter the same), —$X^a$—O—, —CO—$X^a$—, —$X^a$—CO—, —$CONR^a$—$X^a$—, —$X^a$—$CONR^a$—, —$NR^aCO$—$X^a$—, —$X^a$—$NR^aCO$—, —S—$X^a$—, —$X^a$—S—, —SO—$X^a$—, —$X^a$—SO—, —$NR^a$—$X^a$—, —$X^a$—$NR^a$—, —$SO_2$—$X^a$—, —$X^a$—$SO_2$—, —C(=N—$CO_2$—$R^1$)—, —C(=N—$SO_2$—$R^1$)—, —C(=N—$SO_2NH_2$)—, —C(=CH—$NO_2$)—, —C(=N—CN)—, or $C_{3-8}$ cycloalkylidene optionally having substituent(s); preferably a bond, —NH—, —$NR^1$—, —CO—, —$CO_2$—, —OCO—, —$CONR^a$—, —$NR^aCO$—, —$NR^2CONR^3$—, an oxygen atom, a sulfur atom, —SO—, —$SO_2$—, —$NR^aSO_2$—, —$SO_2NR^a$—, $C_{2-6}$ alkenylene optionally having substituent(s), —CO—$X^a$—, —$X^a$—CO—, —$CONR^a$—$X^a$—, —$X^a$—$CONR^a$—, —$NR^aCO$—$X^a$—, —$X^a$—$NR^aCO$— or $C_{3-8}$ cycloalkylidene optionally having substituent(s);

more preferably a bond, —CO—, —$CONR^a$—, —$NR^aCO$—, —CO—$X^a$—, —$X^a$—CO—, —$CONR^a$—$X^a$—, —$X^a$—$CONR^a$—, —$NR^aCO$—$X^a$— or —$X^a$—$NR^aCO$—.

It is furthermore preferably a bond, —CO—, —CO—$X^a$—, —$X^a$—CO—, —$NR^aCO$—$X^a$— or —$X^a$—$NR^aCO$—, still more preferably a bond, —CO— or —CO—$X^a$—, and yet more preferably —CO—$X^a$— or —$X^a$—CO—.

$R^1$ is $C_{1-6}$ alkyl optionally having substituent(s), preferably $C_{1-3}$ alkyl; $R^2$ and $R^3$ are the same or different and each is a hydrogen atom or $C_{1-6}$ alkyl optionally having substituent(s), preferably a hydrogen atom or $C_{1-3}$ alkyl; $R^a$ is a hydrogen atom or $C_{1-6}$ alkyl optionally having substituent(s), preferably a hydrogen atom or $C_{1-3}$ alkyl; and $X^a$ is $C_{1-6}$ alkylene optionally having substituent(s), preferably $C_{1-3}$ alkylene.

Y is a bond, —NH—, —$NR^4$— (wherein $R^4$ is $C_{1-6}$ alkyl optionally having substituent(s), hereinafter the same), —CO—, —$CO_2$—, —OCO—, —$CONR^b$— (wherein $R^b$ is a hydrogen atom or $C_{1-6}$ alkyl optionally having substituent(s), hereinafter the same), —$NR^bCO$—, —$NR^5CONR^6$— (wherein $R^5$ and $R^6$ are the same or different and each is a hydrogen atom or $C_{1-6}$ alkyl optionally having substituent(s), or $R^5$ and $R^6$ are optionally joined to optionally form, together with atoms bonded thereto, a ring optionally having substituent(s), hereinafter the same), an oxygen atom, a sulfur atom, —SO—, —$SO_2$—, —$NR^bSO_2$—, —$SO_2NR^b$—, $C_{1-6}$ alkylene optionally having substituent(s), $C_{2-6}$ alkenylene optionally having substituent(s), $C_{2-6}$ alkynylene optionally having substituent(s), —O—$X^b$— (wherein $X^b$ is $C_{1-6}$ alkylene optionally having substituent(s), hereinafter the same), —$X^b$—O—, —CO—$X^b$—, —$X^b$—CO—, —$CONR^b$—$X^b$—, —$X^b$—$CONR^b$—, —$NR^bCO$—$X^b$—, —$X^b$—$NR^bCO$—, —S—$X^b$—, —$X^b$—S—, —SO—$X^b$—, —$X^b$—SO—, —$NR^b$—$X^b$—, —$X^b$—$NR^b$—, —$SO_2$—$X^b$—, —$X^b$—$SO_2$—, —C(=N—$CO_2$—$R^4$)—, —C(=N—$SO_2$—$R^4$)—, —C(=N—$SO_2NH_2$)—, —C(=CH—$NO_2$)— or —C(=N—CN)—;

preferably a bond, —NH—, —$NR^4$—, —CO—, —$CO_2$—, —OCO—, —$CONR^b$—, —$NR^bCO$—, —$NR^5CONR^6$—, an oxygen atom, a sulfur atom, —SO—, —$SO_2$—, —$NR^bSO_2$—, —$SO_2NR^b$—, —CO—$X^b$—, —$X^b$—CO—, —$CONR^b$—$X^b$—, —$X^b$—$CONR^b$—, —$NR^bCO$—$X^b$— or —$X^b$—$NR^bCO$—;

more preferably a bond, —CO—, —$CONR^b$—, —$NR^bCO$—, —CO—$X^b$—, —$X^b$—CO—, —$CONR^b$—$X^b$—, —$X^b$—$CONR^b$—, —$NR^bCO$—$X^b$— or —$X^b$—$NR^bCO$—.

It is furthermore preferably a bond, —CO—, —CO—$X^b$—, —$X^b$—CO—, —$NR^bCO$—$X^b$— or —$X^b$—

$NR^bCO-$, still more preferably a bond, —CO—, —CO—$X^b$— or —$X^b$—CO—, yet more preferably a bond, —CO—$X^b$— or —$X^b$—CO—, further more preferably a bond.

$R^4$ is $C_{1-6}$ alkyl optionally having substituent(s), preferably $C_{1-3}$ alkyl; $R^5$ and $R^6$ are the same or different and each is a hydrogen atom or $C_{1-6}$ alkyl optionally having substituent(s), preferably a hydrogen atom or $C_{1-3}$ alkyl; $R^b$ is a hydrogen atom or $C_{1-6}$ alkyl optionally having substituent(s), preferably a hydrogen atom or $C_{1-3}$ alkyl; and $X^b$ is $C_{1-6}$ alkylene optionally having substituent(s), preferably $C_{1-3}$ alkylene.

Z is a hydrogen atom, a halogen atom, $C_{1-6}$ alkyl optionally having substituent(s), $C_{3-8}$ cycloalkyl optionally having substituent(s), aryl optionally having substituent(s), a heterocyclic group optionally having substituent(s), hydroxy, nitro, amino, cyano, $C_{1-6}$ alkoxy optionally having substituent(s), mono- or di-$C_6$ alkylamino optionally having substituent(s), $C_{1-7}$ acylamino optionally having substituent(s), sulfonylamino optionally having substituent(s), hydrazino optionally having substituent(s), guanidino optionally having substituent(s), or amidino optionally having substituent(s); preferably a hydrogen atom, a halogen atom, $C_{1-6}$ alkyl optionally having substituent(s), $C_{3-8}$ cycloalkyl optionally having substituent(s), aryl optionally having substituent(s), a heterocyclic group optionally having substituent(s), hydroxy, nitro, amino, cyano, $C_{1-6}$ alkoxy optionally having substituent(s), mono- or di-$C_{1-6}$ alkylamino optionally having substituent(s), $C_{1-7}$ acylamino optionally having substituent(s), sulfonylamino optionally having substituent(s), hydrazino optionally having substituent(s), guanidino optionally having substituent(s), or amidino optionally having substituent(s); more preferably a hydrogen atom, hydroxy, amino, $C_{1-6}$ alkyl optionally having substituent(s), $C_{1-6}$ alkoxy optionally having substituent(s), aryl optionally having substituent(s) or a heterocyclic group optionally having substituent(s).

It is furthermore preferably a hydrogen atom, hydroxy or amino, still more preferably hydroxy or amino. A still more preferable embodiment is hydroxy. Another still more preferable embodiment is amino.

Preferable examples of the group represented by Z—Y—X— include a hydrogen atom, carboxyl, carboxymethyl, amino, carbamoyl, carbamoylmethyl, (2-amino-2-oxoethyl)aminocarbonyl and the like.

As the compound represented by the formula (1), a compound represented by the formula (1a)

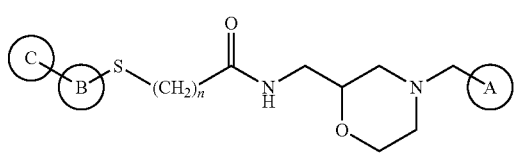

(1a)

[wherein ring C is aryl optionally having substituent(s) or heteroaryl optionally having substituent(s), and other symbols are as defined above], is also preferable.

In the formula (1a), ring C is preferably phenyl, pyridyl, optionally partially hydrogenated 1,2,4-oxadiazolyl, 1,2,4-triazolyl, tetrazolyl, isoxazolyl or the like.

The substituent of ring C is preferably $C_{1-6}$ alkyl, $C_{1-6}$ alkoxy, hydroxy, nitro, amino, cyano, carboxy, $C_{1-6}$ alkoxycarbonyl, carbamoyl, oxo or the like, more preferably methoxy, hydroxy, amino, carboxy, methyl, carbamoyl or oxo.

More specific and preferable examples of the compound represented by the formula (1) or a pharmaceutically acceptable salt thereof include (2S)-[4-(carboxymethyl)thiazol-2-ylthio]-N-{[4-(3,4-dichlorobenzyl)morpholin-2-yl]methyl}acetamide, (2S)-[4-(carboxymethyl)thiazol-2-ylthio]-N-{[4-(3,4-dichlorobenzyl)morpholin-2-yl]methyl}acetamide hydrobromide, (2S)-[4-(3-aminophenyl)thiazol-2-ylthio]-N-{[4-(3,4-dichlorobenzyl)morpholin-2-yl]methyl}acetamide, (2S)-[4-(3-carbamoyl-4-hydroxyphenyl)thiazol-2-ylthio]-N-{[4-(3,4-dichlorobenzyl)morpholin-2-yl]methyl}acetamide, (2S)—N-{[4-(3,4-dichlorobenzyl)morpholin-2-yl]methyl}-[4-(pyridin-4-yl) thiazol-2-ylthio]acetamide, (2S)—N-{[4-(3,4-dichlorobenzyl)morpholin-2-yl]methyl}-[4-(3,4-dimethoxyphenyl)thiazol-2-ylthio]acetamide, (2S)-(4-carbamoylthiazol-2-ylthio)-N-{[4-(3,4-dichlorobenzyl)morpholin-2-yl]methyl}acetamide, (2S)-{4-[(2-amino-2-oxoethyl)aminocarbonyl]thiazol-2-ylthio}-N-{[4-(3,4-dichlorobenzyl)morpholin-2-yl]methyl}acetamide, (2S)—N-{[4-(3,4-dichlorobenzyl)morpholin-2-yl]methyl}-[4-(5-methyl-1,2,4-oxadiazol-3-yl)thiazol-2-ylthio]acetamide hydrochloride, (2S)-(5-amino-8H-indeno[1,2-d]thiazol-2-ylthio)-N-{[4-(3,4-dichlorobenzyl)morpholin-2-yl]methyl}acetamide, (2S)-(4-carboxyphenylthio)-N-{[4-(3,4-dichlorobenzyl)morpholin-2-yl]methyl}acetamide, (2S)-{4-[(2-amino-2-oxoethyl)aminocarbonyl]phenylthio}-N-{[4-(3,4-dichlorobenzyl)morpholin-2-yl]methyl}acetamide, (2S)-{4-[(2-carboxyethyl)aminocarbonyl]thiazol-2-ylthio}-N-{[4-(3,4-dichlorobenzyl)morpholin-2-yl]methyl}acetamide hydrochloride, (2S)-(5-acetamino-1,3,4-thiadiazol-2-ylthio)-N-{[4-(3,4-dichlorobenzyl) morpholin-2-yl]methyl}acetamide, (2S)-4-(4-carbamoylthiazol-2-ylthio)-N-{[4-(3,4-dichlorobenzyl)morpholin-2-yl]methyl}butylamide hydrochloride, (2S)—N-{[4-(3,4-dichlorobenzyl)morpholin-2-yl]methyl}-[4-(1H-tetrazol-5-yl) thiazol-2-ylthio]acetamide, (2S)—N-{[4-(3,4-dichlorobenzyl)morpholin-2-yl]methyl}-([1,3]thiazolo[5,4-b]pyridin-2-ylthio) acetamide, (2S)-(E)-[4-(2-carbamoylethen-1-yl)thiazol-2-ylthio]-N-{[4-(3,4-dichlorobenzyl)morpholin-2-yl]methyl}acetamide, (2S)-[4-(carbamoylmethyl)thiazol-2-ylthio]-N-{[4-(3,4-fluorobenzyl) morpholin-2-yl]methyl}acetamide, (2S)-[4-(carbamoylmethyl)thiazol-2-ylthio]-N-{[4-(4-fluorobenzyl)morpholin-2-yl]methyl}acetamide, (2S)-(4-carboxy-5-methylthiazol-2-ylthio)-N-{[4-(3,4-dichlorobenzyl)morpholin-2-yl]methyl}acetamide, (2S)-(4-carbamoyl-5-methylthiazol-2-ylthio)-N-{[4-(3,4-dichlorobenzyl)morpholin-2-yl]methyl}acetamide, (2S)-(4-carbamoylthiazol-2-ylthio)-N-{[4-(3-chloro-4-fluorobenzyl)morpholin-2-yl]methyl}acetamide, (2S)-[4-(2-amino-2-oxoethyl)aminocarbonylthiazol-2-ylthio]-N-{[4-(3,4-difluorobenzyl)morpholin-2-yl]methyl}acetamide, (2S)-(5-amino-1,3,4-thiadiazol-2-ylthio)-N-{[4-(3-chlorobenzyl)morpholin-2-yl]methyl}acetamide, (2S)-(5-amino-1,3,4-thiadiazol-2-ylthio)-N-{[4-(3,4-difluorobenzyl)morpholin-2-yl]methyl}acetamide, (2S)—N-{[4-(3,4-dichlorobenzyl)morpholin-2-yl]methyl}-(pyrimidin-2-ylthio) acetamide, (2S)-(3-acetyl-2-oxo-2H-chromen-6-ylthio)-N-{[4-(3,4-dichlorobenzyl)morpholin-2-yl]methyl}acetamide,
(2S)—N-{[4-(3,4-difluorobenzyl)morpholin-2-yl]methyl}-(6-oxo-1,6-dihydropyridazin-3-ylthio) acetamide,
(2S)-[6-(carbamoylmethyl)pyrazin-2-ylthio]-N-{[4-(3,4-dichlorobenzyl)morpholin-2-yl]methyl}acetamide, and
(2S)-4-(cyclopentanesulfonyl)-N-{[4-(3-chloro-4-fluorobenzyl)morpholin-2-yl]methyl}butylamide.

A more preferable compound is, for example, (2S)-[4-(carboxymethyl)thiazol-2-ylthio]-N-{[4-(3,4-dichlorobenzyl)morpholin-2-yl]methyl}acetamide, (2S)-[4-(carboxymethyl)thiazol-2-ylthio]-N-{[4-(3,4-dichlorobenzyl)morpholin-2-yl]methyl}acetamide hydrobromide, (2S)-[4-(2-carboxypropan-2-yl)thiazol-2-ylthio]-N-{[4-(3,4-dichlorobenzyl)morpholin-2-yl]methyl}acetamide, (2S)-(5-amino-1,3,4-thiadiazol-2-ylthio)-N-{[4-(3,4-difluorobenzyl)morpholin-2-yl]methyl}acetamide, or (2S)—N-{[4-(3,4-difluorobenzyl)morpholin-2-yl]methyl}-(6-oxo-1,6-dihydropyridazin-3-ylthio)acetamide, and a more preferable compound is, for example, (2S)-[4-(carboxymethyl)thiazol-2-ylthio]-N-{[4-(3,4-dichlorobenzyl)morpholin-2-yl]methyl}acetamide hydrobromide.

The compound of the formula (1) and a pharmaceutically acceptable salt thereof may exist in the form of a hydrate or a solvate (e.g., ethanol solvate etc.), and these hydrates and solvates are also encompassed in the present invention. Since the compound of the formula (1) contains an asymmetric atom, at least two kinds of optical isomers are present. These optical isomers and racemates thereof are encompassed in the present invention.

The compound of the formula (1) and a pharmaceutically acceptable salt thereof can be synthesized by a method known to those of ordinary skill in the art of organic synthesis, a method analogous to the methods described in WO 2006/028284 and WO 2008/007691 (these documents are quoted herein by reference) and the like.

Examples of the pharmaceutically acceptable salt of the compound of the formula (1) include an acid addition salt with an inorganic acid or organic acid and a base addition salt with an inorganic base or organic base, and the compound of the formula (1) can be converted to a salt by treating with an inorganic acid, organic acid, inorganic base or organic base by a conventional method, or according to the method described in WO 2008/007691. In addition, hydrate and solvate of the compound of the formula (1) are also included in the present invention and can be produced by a well-known method.

Examples of the pharmaceutically acceptable salt of the compound of the formula (1) include hydrochloride, hydrobromide, potassium salt and the like, and a preferable example is hydrobromide.

The thus-obtained compound of the present invention or a pharmaceutically acceptable salt thereof can be isolated and purified by a conventional method such as recrystallization, column chromatography and the like. When the obtained product is a racemate, for example, it can be resolved into a desired optically active form by fractional recrystallization of a salt with an optically active acid, or by passing through a column filled with an optically active carrier. Individual diastereomer can be separated by a means such as fractional crystallization, column chromatography and the like. These can also be obtained by using an optically active starting compound and the like. In addition, stereoisomer can be isolated by recrystallization, column chromatography and the like.

A morpholine compound or a pharmaceutically acceptable salt thereof, which is the active ingredient of the present invention, can be administered orally or parenterally in the form of a pharmaceutical composition or preparation (e.g., tablet, liquid etc.) obtained by mixing the compound of the present invention with a pharmaceutically acceptable carrier (e.g., excipient, binder, disintegrant etc.). A pharmaceutical composition can be formulated according to a general method. Examples of the dosage form suitable for oral administration include tablet, capsule, granule, powder and the like. Examples of the dosage form suitable for parenteral administration include injection, eye drop, eye ointment, plaster, gel, insertion agent and the like. Besides these preparations, the active ingredient of the present invention can also be formulated as a DDS (drug delivery system) preparation such as an intraocular implant preparation, microsphere and the like. Examples of the administration form include oral administration, topical administration to the eye (instillation administration, administration to the interior of conjunctival sac, intravitreal administration, sub-conjunctival administration, sub-Tenon's administration etc.), intravenous administration, transdermal administration and the like, with particular preference given to oral administration.

The dose is determined in consideration of the age, body weight, general health condition, sex, diet, administration time, administration method, clearance rate, drug combination, the level of disease state for which the patient is undergoing treatments at that time, or other factors. The daily dose of the compound of the present invention varies depending on the condition and body weight of the patients, the kind of the compound, administration route and the like. For example, it is orally 0.01-1000 mg/kg body weight/day, which is preferably administered in one to several portions per day; it is parenterally about 0.001-100 mg/kg body weight/day, which is preferably administered in one to several portions per day.

In the present invention, an ophthalmic disease caused by ocular angiogenesis is preferably an ophthalmic disease caused by angiogenesis in cornea, choroid or retina. Examples of the ophthalmic disease caused by ocular angiogenesis include retinopathy of prematurity, diabetic retinopathy, corneal neovascularization, macular degeneration, neovascular glaucoma, choroidal neovascularization, neovascular maculopathy, branch retinal vein occlusion, central retinal vein occlusion, diabetic maculopathy and the like. A preferable example of macular degeneration is age-related macular degeneration, and a more preferable example is wet age-related macular degeneration. In the present invention, moreover, the age-related macular degeneration includes age-related macular degeneration accompanied by subfoveal choroidal neovascularization.

Another preferable embodiment is an ophthalmic disease accompanied by angiogenesis in cornea, choroid or retina, and more preferable examples include each of the above-mentioned diseases accompanied by angiogenesis in cornea, choroid or retina.

In the present invention, treatment means administration of the compound of the present invention to an individual (e.g., mammals including human), who has already developed the disease, for the purpose of curing, relieving, or preventing deterioration, or preventing seizure and the like of the disease, and prophylaxis means administration of the compound of the present invention to a healthy individual (e.g., mammals including human), who has not developed the disease, for the purpose of preventing the onset of the disease.

EXAMPLES

While the present invention is explained in detail in the following by referring to Synthetic Examples and Experimental Examples, the present invention is not limited by the examples in any way.

Synthetic Example 1: Synthesis of (2S)—N-{[4-(3, 4-dichlorobenzyl)morpholin-2-yl]methyl}chloroacetamide 2-{[(2R)-4-(3,4-dichlorobenzyl)morpholin-2-yl]methyl}-1H-isoindole-1,3-(2H)-dione (20.76 kg) was dissolved in 158.4 kg of ethanol, 4.82 kg of hydrazine was added dropwise over 6 min, whereby (2S)-2-aminomethyl-4-(3,4-dichlorobenzyl)morpholine was obtained. To said (2S)-2-aminomethyl-4-(3,4-dichlorobenzyl)morpholine was added 108 kg of toluene, and the mixture was concentrated to the total amount of 60 L, and 246.2 kg of ethanol was added. Thereto was added dropwise a solution of 4.62 kg of oxalic acid in 32.8 kg of ethanol over 1 hr 8 min to give 15.14 kg of (2S)-2-aminomethyl-4-(3,4-dichlorobenzyl)morpholine oxalate.

(2S)-2-aminomethyl-4-(3,4-dichlorobenzyl)morpholine oxalate (14.70 kg) was dissolved in 38.0 kg of t-butylmethylether and 36.8 kg of water. Thereto was added dropwise 19.96 kg of 8N aqueous potassium hydroxide solution over 20 min. After separation of the reaction mixture into an organic layer and an aqueous layer, the aqueous layer was discarded. To the resulting organic layer were added 44.2 kg of water, and 4.40 kg of sodium hydrogen carbonate, 5.46 kg of chloroacetyl chloride was added dropwise over 22 min to give a solution of (2S)—N-{[4-(3,4-dichlorobenzyl)morpholin-2-yl]methyl}chloroacetamide in t-butylmethyl ether.

Synthetic Example 2: Synthesis of (2S)-[4-(carboxymethyl)thiazol-2-ylthio]-N-{[4-(3,4-dichlorobenzyl)morpholin-2-yl]methyl}acetamide hydrobromide 4-Ethoxycarbonylmethyl-2-mercaptothiazole (8.18 kg) was dissolved in a mixed solvent of 22.80 kg of t-butanol and 25.72 kg of water, 13.2 kg of 8N sodium hydroxide was added dropwise over 15 min, and the mixture was stirred for 1 hr. Thereto was added the total amount of the solution of (2S)—N-{[4-(3,4-dichlorobenzyl)morpholin-2-yl]methyl}chloroacetamide in t-butylmethyl ether obtained in the above-mentioned Synthetic Example 1, whereby (2S)-[4-(carboxymethyl)thiazol-2-ylthio]-N-{[4-(3,4-dichlorobenzyl)morpholin-2-yl]methyl}acetamide was obtained. To said (2S)-[4-(carboxymethyl)thiazol-2-ylthio]-N-{[4-(3, 4-dichlorobenzyl)morpholin-2-yl]methyl}acetamide was added 68.4 kg of t-butanol, and the mixture was concentrated to the total amount of 44 L, and 81.0 kg of acetonitrile was added thereto. Thereto was added dropwise 6.8 kg of hydrobromic acid over 33 min, and the mixture was stirred and 7.35 kg of t-butanol was added over 5 min. In 15 min from the addition, precipitation of the crystal of (2S)-[4-(carboxymethyl)thiazol-2-ylthio]-N-{[4-(3,4-dichlorobenzyl)morpholin-2-yl]methyl}acetamide hydrobromide began, whereby 17.16 kg of the crystals were finally recovered.

Experimental Example 1: Treatment Effect Relating to Angiogenesis

Using a mouse model experimentally induced to show choroidal neovascularization (hereinafter to be referred to as "CNV") by laser irradiation (CNV model), efficacy relative to the CNV area was evaluated. The CNV model shows migration of macrophage by induction of inflammation by laser irradiation. As a result, VEGF is produced, and a new blood vessel is developed. Therefore, the CNV model is an experimental model showing the efficacy on a disease associated with ocular angiogenesis via VEGF.

Using (2S)-[4-(carboxymethyl)thiazol-2-ylthio]-N-{[4-(3,4-dichlorobenzyl)morpholin-2-yl]methyl}acetamide hydrobromide as a test compound, the following experiment was performed.

(Method)

Laser was irradiated (6 spot irradiation) on one eye of male C57BL/6J mouse (7-week-old) to experimentally induce CNV.

The mouse was intramuscularly administered (1 mL/kg) with a ketamine hydrochloride/xylazine hydrochloride (1:1, v/v) mixed solution into the thigh and, after systemic anesthesia, mydriasis was induced with mydriatic eye drops, and laser irradiation (wavelength 532 nm, spot size 50 μm, irradiation time 0.1 second, laser output 120 mW) was performed at 6 points while avoiding thick capillary in the retina. A control antibody and an anti-mouse VEGF antibody (purchased from R&D Systems, Inc.) were intravitreally (2 L/eye) administered only once immediately after laser irradiation. Based on the most recent body weight, a prepared test liquid of the test compound was orally administered using a sonde at 0.1 mL/10 g (medium: 0.5% hydroxypropylmethylcellulose). After confirmation of sufficient recovery from the anesthesia of the test animal after laser irradiation, the test liquid was orally administered once per day only on the laser-induction day, and repeatedly administered orally twice per day from the next day of laser irradiation to one day before the final day. The number of cases was 14 animals/group and, as described in Table 1, not less than 10 cases in number were secured per group.

TABLE 1

| group No. | group name | administration method | administration dose | number of cases (mice) |
|---|---|---|---|---|
| 1 | control antibody | intravitreal | 20 ng/eye | 11 |
| 2 | anti-mouse VEGF antibody | intravitreal | 20 ng/eye | 13 |
| 3 | medium | oral | — | 12 |
| 4 | test compound | oral | 20 mg/kg | 12 |

At 7 days from the laser irradiation, under systemic anesthesia by intramuscular administration (1 mL/kg) of a ketamine hydrochloride/xylazine hydrochloride (1:1, v/v) mixed solution into the thigh, a 4% FITC-dextran solution was administered at 0.5 mL/animal from the tail vein. After euthanasia, the eyeball was removed, fixed with 4% paraformaldehyde-phosphate buffer, and flat mount specimen were prepare according to a conventional method. Using a confocal microscope (OLYMPUS FV-1000D; magnification: ×20, number of pixels: 512 pixel×512 pixel), CNV site in a flat mount specimen was photographed, and measured using an image analysis software (NIH ImageJ). The area is expressed in pixel. As the statistical method for each group, t-test was performed between the first group and the second group, and the third group and the fourth group, by using each individual value, and a significant level of each side was set to $p<0.05$.

(Results)

The CNV area after 7 days from laser irradiation is shown in FIG. 1. A significant CNV suppressive action was found in the anti-mouse VEGF antibody intravitreal administration group, as compared to the control antibody intravitreal administration group. In the test compound oral administration group, a significant CNV suppressive effect was observed as compared to the only vehicle oral administration group. From these results, since anti-mouse VEGF antibody was significantly suppressed in CNV experimentally induced by laser irradiation, involvement of VEGF was shown. Also, since the test compound showed a significant suppressive effect on CNV of this model by repeated oral administration, a morpholine compound represented by the test compound was shown to inhibit CNV.

Experimental Example 2: Inhibitory Effect on Migration of Human Vascular Endothelial Cells Using (2S)-[4-(carboxymethyl)thiazol-2-ylthio]-N-{[4-(3,4-dichlorobenzyl)morpholin-2-yl]methyl}acetamide hydrobromide as a test compound, an inhibitory effect on the migration of human vascular endothelial cells, which is induced by a ligand of human CCR3 (e.g., human CCL11, human CCL24, human CCL26 and the like), is evaluated.

It is considered that migration of vascular endothelial cells occurs in the process of development of angiogenesis, and a compound that inhibits migration of vascular endothelial cells is considered to be useful as a therapeutic agent for a disease caused by angiogenesis, for example, an ophthalmic disease caused by ocular angiogenesis.

INDUSTRIAL APPLICABILITY

Since the compound of the present invention suppresses ocular angiogenesis, it is considered to be useful as a therapeutic agent or prophylactic agent for an ophthalmic disease caused by ocular angiogenesis, specifically retinopathy of prematurity, diabetic retinopathy, corneal neovascularization, macular degeneration, neovascular glaucoma, choroidal neovascularization, neovascular maculopathy, branch retinal vein occlusion, central retinal vein occlusion, diabetic maculopathy and the like.

This application is based on patent application No. 2013-153878 filed in Japan, the contents of which are incorporated in full herein.

The invention claimed is:

1. A method of treating an ophthalmic disease caused by ocular angiogenesis selected from the group consisting of macular degeneration and choroidal neovascularization disease, comprising administering an effective amount of (2S)-[4-(carboxymethyl)thiazol-2-ylthio]-N-{[4-(3,4-dichlorobenzyl)morpholin-2-yl]methyl}acetamide having the following formula

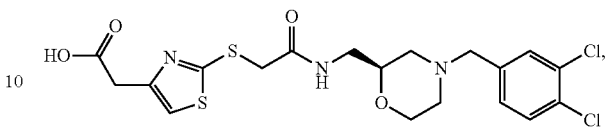

or a pharmaceutically acceptable salt thereof to an animal.

2. The method according to claim 1, wherein the (2S)-[4-(carboxymethyl)thiazol-2-ylthio]-N-{[4-(3,4-dichlorobenzyl)morpholin-2-yl]methyl}acetamide or a pharmaceutically acceptable salt thereof is (2S)-[4-(carboxymethyl)thiazol-2-ylthio]-N-{[4-(3,4-dichlorobenzyl)morpholin-2-yl]methyl}acetamide hydrobromide.

3. The method according to claim 1, wherein the ophthalmic disease caused by ocular angiogenesis is choroidal neovascularization disease.

4. The method according to claim 1, wherein the ophthalmic disease caused by ocular angiogenesis is macular degeneration.

5. The method according to claim 1, wherein the ophthalmic disease caused by ocular angiogenesis is age-related macular degeneration.

6. The method according to claim 1, wherein the ophthalmic disease caused by ocular angiogenesis is wet age-related macular degeneration.

7. A method of treating age-related macular degeneration comprising administering an effective amount of (2S)-[4-(carboxymethyl)thiazol-2-ylthio]-N-{[4-(3,4-dichlorobenzyl)morpholin-2-yl]methyl}acetamide hydrobromide as an active ingredient to an animal.

8. A method of treating wet age-related macular degeneration comprising administering an effective amount of (2S)-[4-(carboxymethyl)thiazol-2-ylthio]-N-{[4-(3,4-dichlorobenzyl)morpholin-2-yl]methyl}acetamide hydrobromide as an active ingredient to an animal.

9. The method according to claim 2, wherein the ophthalmic disease caused by ocular angiogenesis is choroidal neovascularization disease.

10. The method according to claim 2, wherein the ophthalmic disease caused by ocular angiogenesis is macular degeneration.

* * * * *